US008809092B2

(12) United States Patent
Linfield et al.

(10) Patent No.: US 8,809,092 B2
(45) Date of Patent: Aug. 19, 2014

(54) GENERATING AND DETECTING RADIATION

(76) Inventors: Edmund Linfield, Leeds (GB); John Cunningham, Leeds (GB); Alexander Giles Davies, Leeds (GB); Christopher Wood, Leeds (GB); Paul John Cannard, Woodbridge (GB); David Graham Moodie, Nr Woodbridge (GB); Xin Chen, Ipswich (GB); Michael James Robertson, Ipswich (GB)

(*) Notice: Subject to any disclaimer, the term of this patent is extended or adjusted under 35 U.S.C. 154(b) by 42 days.

(21) Appl. No.: 13/384,214

(22) PCT Filed: Jul. 19, 2010

(86) PCT No.: PCT/GB2010/051173
§ 371 (c)(1),
(2), (4) Date: Jan. 13, 2012

(87) PCT Pub. No.: WO2011/007185
PCT Pub. Date: Jan. 20, 2011

(65) Prior Publication Data
US 2012/0113417 A1 May 10, 2012

(30) Foreign Application Priority Data
Jul. 17, 2009 (GB) .................................. 0912512.1

(51) Int. Cl.
*H01L 21/00* (2006.01)
(52) U.S. Cl.
USPC .................................. 438/46; 438/45; 438/47
(58) Field of Classification Search
USPC .......... 438/34, 45, 46, 47; 257/192, 194, 199, 257/200
See application file for complete search history.

(56) References Cited

U.S. PATENT DOCUMENTS

| 4,746,620 A | 5/1988 | Diadiuk et al. |
| 4,794,439 A | 12/1988 | Webb et al. |
| 6,903,383 B2 * | 6/2005 | Yokogawa et al. ........... 257/192 |

(Continued)

FOREIGN PATENT DOCUMENTS

| EP | 1 598 695 A2 | 11/2005 |
| GB | 2 393 037 A | 3/2004 |

(Continued)

OTHER PUBLICATIONS

International Preliminary Report on Patentability and Written Opinion, issued in PCT/GB2010/051173, 14 pages, Date of Mailing: Jan. 26, 2012.

(Continued)

*Primary Examiner* — Kevin M Picardat
(74) *Attorney, Agent, or Firm* — Klarquist Sparkman, LLP

(57) ABSTRACT

A method of generating radiation comprises: manufacturing a structure comprising a substrate supporting a layer of InGaAs, InGaAsP, or InGaAlAs material doped with a dopant, said manufacturing comprising growing said layer such that said dopant is incorporated in said layer during growth of the layer; illuminating a portion of a surface of the structure with radiation having photon energies greater than or equal to a band gap of the doped InGaAs, InGaAsP, or InGaAlAs material so as to create electron-hole pairs in the layer of doped material; and accelerating the electrons and holes of said pairs with an electric field so as to generate radiation. In certain embodiments the dopant is Fe. Corresponding radiation detecting apparatus, spectroscopy systems, and antennas are described.

39 Claims, 16 Drawing Sheets

(56) References Cited

U.S. PATENT DOCUMENTS

| | | | |
|---|---|---|---|
| 2004/0207032 A1 | | 10/2004 | Edamura et al. |
| 2007/0120226 A1* | | 5/2007 | Nakaji et al. .............. 257/603 |
| 2009/0057650 A1 | | 3/2009 | Lieber et al. |

FOREIGN PATENT DOCUMENTS

| | | |
|---|---|---|
| JP | 2006-086227 A | 3/2006 |
| WO | WO 00/52766 A1 | 9/2000 |
| WO | WO 2008/054846 A2 | 5/2008 |

OTHER PUBLICATIONS

International Search Report and Written Opinion of the International Searching Authority, mailed Oct. 26, 2010, for corresponding International Application No. PCT/GB2010/051173, 20 pages.

Guézo et al., "Ultrashort, Nonlinear, Optical Time Response of Fe-doped InGaAs/InP Multiple Quantum Wells in 1.55-μm Range," *Appl. Phys. Letters*, vol. 82, No. 11, pp. 1670-1672, Mar. 17, 2003.

Gulwadi et al., "Transition Metal Implants in $In_{0.53}GA_{0.47}A_s$," *J. Appl. Phys.*, vol. 69, No. 8, pp. 4222-4227, Apr. 15, 1991.

Knight et al., "Growth of Semi-insulating InGaAsP Alloys Using Low-pressure MOCVD," *J. Crystal Growth*, vol. 124, pp. 352-357, Nov. 1992.

Shen et al., Generation and Detection of Ultrabroadband Terahertz Radiation Using Photoconductive Emitters and Receivers, *Appl. Phys. Letters*, vol. 85, No. 2, pp. 164-166, Jul. 12, 2004.

Suzuki and Tonouchi, "Fe-implanted InGaAs Terahertz Emitters for 1.56 μm Wavelength Excitation," *Appl. Phys. Letter*, vol. 86, No. 5, pp. 051104-01-051104-03, Jan. 27, 2005.

Suzuki and Tonouchi, "Fe-implanted InGaAs Photoconductive Terahertz Detectors Triggered by 1.56 μm Femtosecond Optical Pulses," *Appl. Phys. Letters*, vol. 86, No. 16, pp. 163504-01-163504-03, Apr. 15, 2005.

Upadhya et al., "Ultra-broadband Coherent Terahertz Spectroscopy Using Asymmetric Excitation of Photoconductive Structures," *$TH_z$ Technology, Ultrafast Measurements, and Imaging*, 2005 Joint 30th Intl. Conf. on Infrared and Millimeter Waves & 13th Intl. Conf. on Terahertz Electronics, vol. 2, pp. 451-452, Sep. 19, 2005.

Wolf et al., "Semi-insulating Fe-and Ti-doped InP and InGaAs for Ultrafast Infrared Detectors Grown by LP-MOCVD," Paper presented at 6th Conf. on Semi-insulating III-V Materials, Toronto, Canada, pp. 131-136, Jan. 1, 1990.

Wood et al., "THz Generation Using 800 to 1550 nm Excitation of Photoconductors," Infrared, Millimeter and Terahertz Waves, 2009, 34th International Conference on IEEE, Piscataway, New Jersey, pp. 1-3, Sep. 21, 2009.

Wood et al., "Terahertz Emission from Metal-Organic Chemical Vapor Deposition Grown Fe:InGaAs using 830 nm to 1.55 μm Excitation," *Appl. Phys. Letters*, vol. 96, pp. 194104-1-194104-3, May 14, 2010.

Search Report for Great Britain App. No. 0912512.1, dated Dec. 18, 2009, 4 pp.

\* cited by examiner

GENERATING AND DETECTING RADIATION

CROSS REFERENCE TO RELATED APPLICATIONS

This is the U.S. National Stage of International Application No. PCT/GB2010/051173, filed Jul. 19, 2010, which in turn claims the benefit of Great Britain Application No. GB0912512.1, filed Jul. 17, 2009.

FIELD OF THE INVENTION

The present invention relates generally to the generation, detection and use of radiation, and in particular, although not exclusively, to the generation, detection, and use of THz radiation.

BACKGROUND TO THE INVENTION

The generation, detection, and use of THz radiation (that is radiation having frequencies in the range 50 GHz-20 THz) is known. One application utilising the generation and detection of THz radiation is THz time-domain spectroscopy. This is a spectroscopic technique in which short pulses of THz radiation are generated and used to probe material properties. The generated THz pulses are directed towards a sample of the material or the object to be probed, and the radiation subsequently transmitted through the sample or object, or reflected from the sample or object is detected. The use of THz radiation has several advantages over other forms of spectroscopy. These include the fact that many materials are transparent to THz radiation, THz radiation is safe for biological tissues, and images formed with THz radiation can have good resolution (for example less than 1 mm). Also, many potentially interesting materials have unique spectral fingerprints in the THz range, which means that THz radiation can be used to identify them. These materials include certain types of explosives, and compounds used in commercial medicines and certain illegal substances. As many materials are transparent to THz radiation, the items of interest can be observed through visually opaque intervening layers, such as packaging and clothing.

Typically, THz pulses are generated by a short pulsed laser, and last only a few picoseconds. Known techniques for generating THz pulses include surface emission from a semiconductor surface illuminated by an ultra-short optical pulse, and emission from a voltage biased photoconductive emitter; in both cases the optical laser pulse creates electron-hole pairs in a semiconductor material which may be accelerated to generate THz radiation. Another technique is optical rectification, in which short laser pulses pass through a transparent crystal material which then emits a THz pulse without any applied voltages.

A variety of techniques are also known for the detection of THz pulses, including photoconductive detection, in which an electrical current is produced between a pair of electrodes (or antenna leads). This current is generated by the THz electric field pulses acting on electrons/holes pairs which have been themselves been excited by a short laser pulse.focused onto a semiconductor surface. After the THz electric field generates a current across the antenna leads, this may then be amplified using a suitably arranged amplifier. Another method of detecting THz pulses is electro-optical sampling.

While terahertz time-domain spectroscopy (THz-TDS) is a widely-used technique applicable to the study of many systems, and its usefulness as a non-destructive tool for spectroscopy, imaging, monitoring, and detection of materials has been demonstrated across many application areas, laboratory-based systems are typically large, cumbersome and expensive. This is owing primarily to the Ti:sapphire laser (centre wavelength 800 nm) used to provide pulsed excitation with sufficient energy to exceed the band-gap of the most common semiconductor system used for THz emission, gallium arsenide. THz emission from alternative materials with smaller band-gaps than gallium arsenide could in principle provide a compelling solution to these problems, allowing more portable THz spectroscopy systems to be made.

Materials with potentially suitable, smaller band-gaps include InAs, InGaAs, and InAlAs. However, a problem in trying to use these materials for the generation of THz radiation is that, when grown, these materials tend to have low resistivities. As will be appreciated, in typical techniques for generating THz radiation, relatively large bias voltages or potentials (some tens of volts) are applied between electrodes, to accelerate the electrons and holes of the electron-hole pairs excited in the semiconductor material by incident illuminating radiation with photon energies greater than the relevant band-gap. If the resistivities of the semiconductor materials are low, then the application of these bias voltages (or equivalently these bias electric fields) drives unacceptably large currents between the electrodes, through the semiconductor material, causing it to be damaged.

As a result of these problems, there remains the need for methods and apparatus for THz emission from materials excited by telecoms wavelengths, which would allow comparatively cheap 1.55 micron wavelength lasers to replace the Ti:sapphire laser, for example.

SUMMARY OF THE INVENTION

It is an aim of certain embodiments of the invention to obviate, mitigate against, or solve, at least partly, one or more of the problems associated with the prior art. Certain embodiments aimed to provide methods and apparatus for generating THz radiation using materials excited by telecoms wavelengths, and in particular wavelengths of 1.55 microns.

According to a first aspect of the present invention, there is provided a method of generating radiation, the method comprising:

manufacturing a structure comprising a substrate supporting a layer of InGaAs, InGaAsP, or InGaAlAs material doped with a dopant (e.g. a layer of Fe-doped InGaAs or Fe-doped InGaAsP material), said manufacturing comprising growing said layer such that said dopant is incorporated in said layer during growth of the layer;

illuminating a portion of a surface of the structure with radiation having photon energies greater than or equal to a band gap of the doped material (e.g. Fe-doped InGaAs or Fe-doped InGaAsP material) so as to create electron-hole pairs in the layer of doped material; and accelerating the electrons and holes of said pairs with an electric field so as to generate radiation.

It will be appreciated that the structure may also be referred to as a wafer structure, a multilayer structure, a multilayer semiconductor structure, an antenna structure, a photoconductive antenna, or simply an antenna.

Typically, the electric field will accelerate the electrons and holes in opposite directions, such that the resulting changing dipoles generate the radiation.

It will thus be appreciated that a key feature in the method of this first aspect of the invention is that the doped semiconductive material has been produced by a growth technique, such that the dopant (e.g. Fe) is incorporated in the structure during the growth process. By incorporating the dopant in this manner, the material of the layer is able to be lattice-matched with the substrate. The incorporation of the dopant in this manner (during growth) results in the semiconductor material still having a band-gap that is suitable for excitation of electron-hole pairs using so-called "telecoms wavelengths" (e.g. 1550 nm), but the presence of the dopant (e.g. Fe) in the grown layer provides the layer material with substantially increased resistivity compared with the un-doped material. In certain embodiments, this enables relatively high bias voltages or potentials to be applied, without driving unacceptably high currents across the electrodes.

An advantage of producing the doped layer using a growth technique is that the amount of dopant incorporated can be precisely and reproducibly controlled. This is in contrast to other potential techniques for introducing Fe, for example, into a previously un-doped layer of InGaAsP or InGaAs material, for example by Fe implantation or heavy-ion irradiation. These alternative techniques produce characteristic damage to the semiconductor structure, lead to different, characteristic concentration profiles of the dopant material, and are unable to provide the same degree of control of the quantity Fe incorporated in the semiconductor layer as is achievable in embodiments of the invention where the Fe is incorporated during growth of the layer.

It will be appreciated that a grown, doped water (e.g. a grown InGaAs:Fe wafer) will have an identifiably different and characteristic structure compared with a corresponding wafer produced by alternative techniques, such as post-growth implantation. These different characteristics will generally include different dopant concentration profiles and different microscopic appearances. In other words, it will be appreciated that a skilled person will readily be able to identify whether an Fe-doped InGaAs or InGaAsP layer, or other doped semiconductive layer, has been produced by growth or other techniques, by making one or more of a variety of known measurements or observations.

In certain embodiments, the dopant is an element. In certain embodiments the dopant is a transition metal element. In certain embodiments the dopant is chromium, in others vanadium, and in others iron (Fe).

In certain embodiments, the generated carriers (i.e. the electron-hole pairs) may be accelerated by an intrinsic electric field and by differences in the electron and hole mobilities (the so-called photo-Dember effect). In such embodiments, the method may further comprise the application of a magnetic field to the structure. This can enhance the generation of radiation, particularly THz radiation, from the excited carriers. However, in certain alternative embodiments, rather than relying on any intrinsic electric field, the method may additionally comprise applying an electric field to accelerate the carriers and so generate the radiation.

In certain embodiments, this acceleration of the carriers may be achieved by applying a voltage (potential difference) between suitably arranged electrodes. These may be arranged at or on a surface of the structure, or alternatively may be embedded within it.

The illuminating radiation may be arranged to illuminate an exposed surface of the layer of material directly, but in alternative embodiments the illuminating radiation may reach the layer through one or more additional layers that are at least partially transparent to the relevant wavelength(s).

In certain embodiments, the generated radiation comprises THz radiation, e.g. radiation having a frequency in the range 0.05 THz to 20 THz.

In certain embodiments, the substrate comprises a single crystal of material, which may also be described as a wafer. Suitable materials for the substrate/single crystal material include InP or Fe doped InP.

In certain embodiments, growing said layer comprises epitaxially growing said layer on the substrate. This may comprise growing said layer directly on the substrate, which may itself be a single crystal, or on one or more intermediate layers, themselves grown on the substrate.

In certain embodiments, said illuminating comprises illuminating said portion with radiation having a wavelength in the range 800 nm to 1700 nm, or in the range 1150 to 1550 nm.

In certain embodiments, said illuminating comprises illuminating said portion with radiation in a direction substantially normal to said layer.

In certain alternative embodiments, said illuminating comprises illuminating said portion with radiation in a direction substantially parallel to said layer.

In certain other embodiments, said illuminating comprises illuminating said portion with radiation in a direction having components normal to and parallel to said layer.

In certain embodiments, the method further comprises applying said electric field to accelerate said electrons and holes. In such embodiments, said structure may comprise a first electrode and a second electrode, and applying said electric field may comprise applying a potential difference between the first and second electrodes. In certain embodiments, said potential difference is an alternating potential difference.

In certain embodiments, the electrodes are arranged to define a gap between them, and said illuminating comprises directing the illuminating radiation at said gap.

In certain embodiments, the electrodes are arranged at a surface of the structure, such that at least portions of the electrodes are exposed. In alternative embodiments, however, one or both of the electrodes may be embedded in the structure.

It will be appreciated that certain embodiments comprise a structure having lateral geometry. Certain embodiments comprise, provide, or utilise a lateral metal-insulator-metal structure. Certain embodiments comprise metal (antenna) electrodes deposited on a bulk semiconductor. Certain embodiments comprise or may be described as photomixers.

Another aspect of the invention provides apparatus for generating radiation, the apparatus comprising:

a structure comprising a substrate supporting a layer of InGaAs, InGaAsP, or InGaAlAs material doped with a dopant (e.g. a layer of Fe-doped InGaAs or Fe-doped InGaAsP material), said layer having been grown such that said dopant has been incorporated in said layer during growth of the layer; and an illumination source arranged to illuminate a portion of a surface of the structure with radiation having photon energies greater than or equal to a band gap of the doped material (e.g. Fe-doped InGaAs or Fe-doped InGaAsP material) so as to create electron-hole pairs in the layer of doped material.

In certain embodiments, the apparatus may utilise at least an intrinsic electric field in the layer to accelerate the excited carriers to generate radiation.

In certain embodiments, the apparatus may further comprise means for applying a magnetic field to the structure.

In certain embodiments, the apparatus further comprises means for applying an electric field to accelerate the electrons and holes of said pairs so as to generate radiation. This means for applying an electric field may, for example, comprises a first electrode and a second electrode, and a voltage source arranged to apply a potential difference between the first and second electrodes.

In certain embodiments, the apparatus further comprises a lens arranged to focus radiation generated by said electron-hole pairs. This lens may be separate from, or may form part of said structure.

In certain embodiments the lens is arranged to focus generated radiation transmitted through the substrate.

In certain embodiments the illumination source is adapted to illuminate said portion with radiation having a wavelength in the range 800 nm to 1700 nm, or 1150 to 1550 nm.

In certain embodiments the illumination source comprises a laser.

Another aspect of the invention provides a spectroscopy method comprising:
    generating radiation using a method in accordance with any aspect of the invention;
    directing the generated radiation at a sample or object; and
    detecting at least one of: generated radiation transmitted through; and generated radiation reflected from the sample or object.

Another aspect of the invention provides spectroscopy apparatus comprising:
    apparatus in accordance with any aspect of the invention, arranged to generate radiation;
    means for directing the generated radiation at a sample or object; and
    detection means for detecting at least one of: generated radiation transmitted through; and generated radiation reflected from a sample or object at which the generated radiation is directed.

Another aspect of the invention provides a method of detecting radiation comprising:
    manufacturing a structure comprising a substrate supporting a layer of InGaAs, InGaAsP, or InGaAlAs material doped with a dopant (e.g. a layer of Fe-doped InGaAs or Fe-doped InGaAsP material), said manufacturing comprising growing said layer such that said dopant is incorporated in said layer during growth of the layer;
    illuminating a portion of a surface of the structure with radiation to be detected, such that photons of said radiation having energies greater than or equal to a band gap of the doped material (e.g. Fe-doped InGaAs or Fe-doped InGaAsP material) create electron-hole pairs in the layer of doped material; and
    detecting an electric field or current generated by said electron-hole pairs.

In certain embodiments, said structure comprises a first electrode and a second electrode, and said detecting comprises detecting a current between the first and second electrodes.

Another aspect of the invention provides apparatus for detecting radiation, the apparatus comprising:
    a structure comprising a substrate supporting a layer of InGaAs, InGaAsP, or InGaAlAs material doped with a dopant (e.g. a layer of Fe-doped InGaAs or Fe-doped InGaAsP material), said layer having been grown such that said dopant has been incorporated in said layer during growth of the layer;
    means for illuminating a portion of a surface of the structure with radiation to be detected, such that photons of said radiation having energies greater than or equal to a band gap of the doped material create electron-hole pairs in the layer of doped material; and
    means for detecting an electric field or current generated by said electron-hole pairs.

In certain embodiments said structure comprises a first electrode and a second electrode, and said means for detecting comprises means for detecting a current between the first and second electrodes.

Another aspect of the invention provides an antenna for generating and/or detecting radiation, the antenna comprising:
    a substrate supporting a layer of InGaAs, InGaAsP, or InGaAlAs material doped with a dopant (e.g. a layer of Fe-doped InGaAs or Fe-doped InGaAsP material), said layer having been grown such that said dopant has been incorporated in said layer during growth of the layer; and
    a first electrode and a second electrode,
    the electrodes being arranged to define a gap between them and being further arranged with respect to said layer such that when radiation is directed at said gap, photons of said radiation having energies greater than or equal to a band gap of the doped material create electron-hole pairs in the layer of doped material, and an electric field may be applied to accelerate the electron-hole pairs and generate radiation by application of a potential difference between the electrodes, and/or an electric current generated by the electron-hole pairs across the electrodes may be detected.

Again, in certain embodiments of these aspects, the dopant is an element. In certain embodiments the dopant is a transition metal element. In certain embodiments the dopant is chromium, in others vanadium, and in others iron (Fe).

Another aspect of the invention provides use of grown, doped InGaAs, InGaAsP, or InGaAlAs material (e.g. grown Fe-doped InGaAs or Fe-doped InGaAsP material) in the generation or detection of radiation, and THz radiation in particular.

BRIEF DESCRIPTION OF THE DRAWINGS

Embodiments of the invention will now be described with reference to the accompanying drawings, of which.

DESCRIPTION OF EMBODIMENTS OF THE INVENTION

Figure 1:
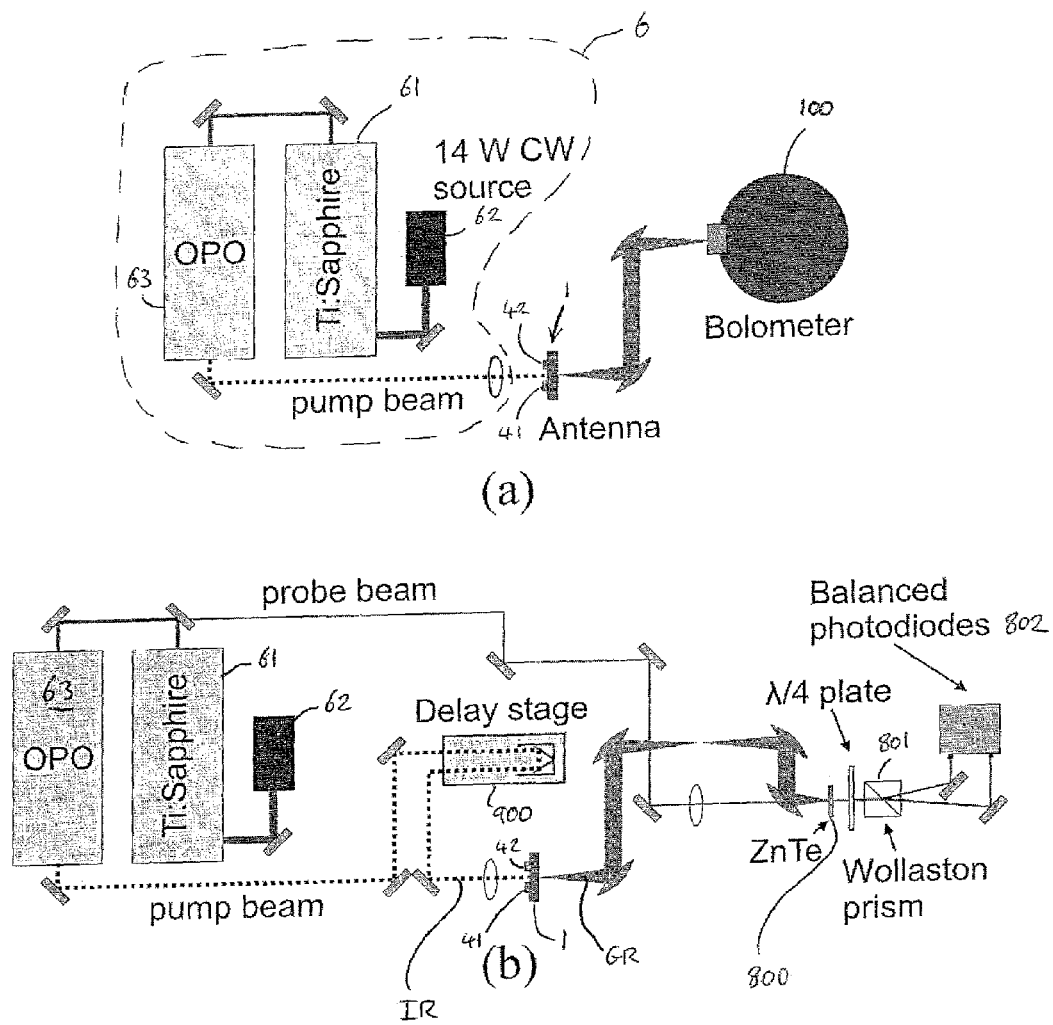
FIG. 1 illustrates THz generation and detection systems embodying the invention, with FIG. 1(a) illustrating the THz optical setup used for helium cooled bolometric detection of THz signals generated from samples using a tunable OPO pump signal, and FIG. 1(b) illustrating a THz-TDS system embodying the invention and based on a tunable OPO pump and a fixed 830 nm Ti:Sapphire probe signal.

In the following description, the use of Fe-doped InGaAs and InGaAsP emitters lattice matched to an Fe:InP substrate, where the Fe doping is introduced during epitaxial growth of the wafer, is described, which allows precise control over the level of doping, and excellent reproducibility between growth runs.

Referring now to FIGS. 1 to 5, initial measurements were performed on two wafer structures embodying the invention; NQS 1940, a Fe:InGaAs emitter, and NQS 2002, an Fe:InGaAsP emitter. Metal-organic chemical vapour deposition (MOCVD) growth of these substrates was conducted at 810 torr (1065 mbar) and 660° C. (the latter determined from a thermocouple measurement), in a horizontal quartz reactor. Before each growth, the susceptor and reactor were conditioned by baking and cleaning to ensure reproducible starting conditions. The precursors were trimethylindium (TMI), trimethylgallium (TMG), and 100% arsine ($AsH_3$). 100% phosphine was also used to form the InP cap and buffer layers. Ferrocene ($Fe(C_5H_5)_2$) from a sublimation bubbler was used as the iron dopant source. All precursors were semiconductor grade or better. Purified $H_2$ was used as the carrier gas and the total gas flow through the reactor during epitaxy was approx 7.0 slpm. $H_2$ was also used for bubbler pickup, dilution, and pusher flows.

Gold electrodes 41,42 were photolithographically defined in a bow-tie pattern on the emitters, with an electrode separation of 400 μm. A THz-TDS system was constructed using an 830 nm, 120 fs pulsewidth Ti:sapphire laser 61 pumped by a 14 W Nd:YAG CW source 62. The laser output was split, and 1.3 W output power was diverted into a cavity-tuned optical parametric oscillator (OPO) 63 containing a quasi-phase matched, periodically poled lithium niobate crystal in linear cavity configuration. The idler output wave, generated by nonlinear interactions within the lithium niobate crystal, was used to pump the emitters, across the wavelength range from 1150 nm to 1550 nm, by altering the cavity length of the OPO. The optical efficiency of the OPO was of order ~10%. This setup was used to test the efficiency of the emitter across the available range of output wavelengths. The OPO output, maintained at 50 mW power for all experiments unless otherwise stated, was focussed onto the photoconductive gap 412 in each emitter 1, across which a 10 kHz alternating bias of 0 to 100 V was applied. The subsequently generated THz radiation was collected in transmission mode via a silicon lens glued to the back of the antenna, and collected by a parabolic mirror. Initial measurements were performed using the arrangement shown in FIG. 1(a), where the THz signal was first collimated, and then focussed into a helium cooled bolometer 100 to measure the absolute THz power generated. Subsequent measurements, depicted in FIG. 1(b), used 140 mW output power from the Ti:sapphire source as a probe, spatially overlapped with the THz signal on a 1 mm thick ZnTe detector crystal 800 for electro-optic detection; in this configuration the probe beam was split after the ZnTe detector into two parts with orthogonal polarisation using a quarter wave plate followed by a Wollaston prism 801, and the respective intensities measured on a pair of balanced photodiodes 802. Introduction of a delay stage 900 into the pump path allowed time-resolved images of the generated THz signal to be obtained using a lock-in amplifier connected to the photodiodes.

The pump wavelength was swept from 1150 nm to 1550 nm in steps of 50 nm, and the power incident on the bolometer measured for each, with further data recorded at 830 nm pump from the Ti:Sapphire laser. The results, shown in FIG. 2, demonstrate THz output for the complete range of pump wavelengths with an optimum pump wavelength of ~1250 nm. The slight dip in power seen at 1450 nm is caused by a reduction in the OPO output power at this wavelength, which induced a normalisation error. The output signal follows the same trend for both wafers, though NQS 2002 clearly outperforms NQS 1940 in terms of output power.

Figure 2:
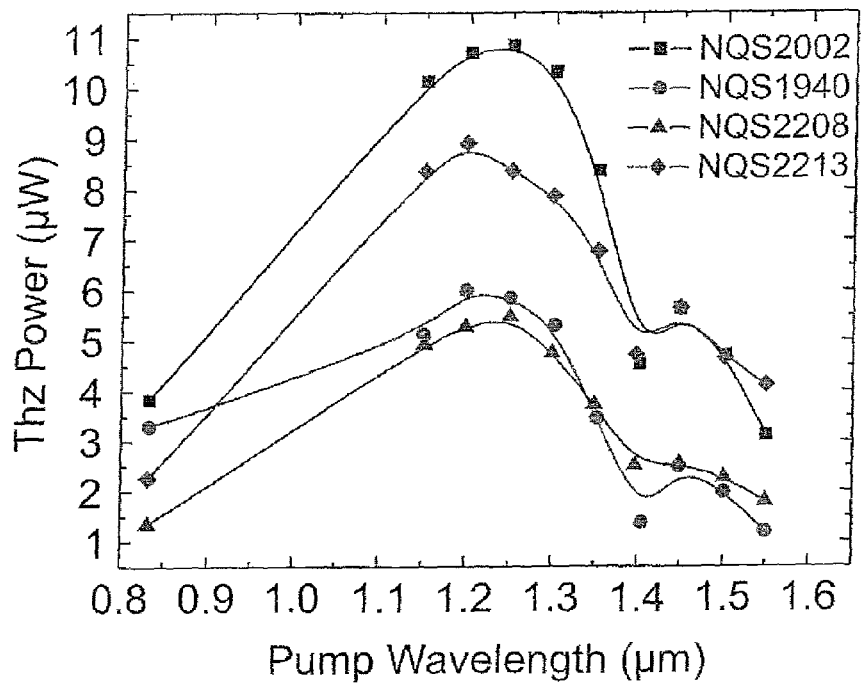
FIG. 2 shows the results of bolometric measurements of THz signals from antennas embodying the present invention and fabricated on wafers of Fe:InGaAs (NQS 1940) and Fe:InGaAsP (NQS 2002), with comparisons made to a repeat growth (sample NQS 2208), equivalent to NQS 1940, and a fourth wafer (NQS 2213), with ~10% the Fe content of NQS 1940/2208.
Figure 3:
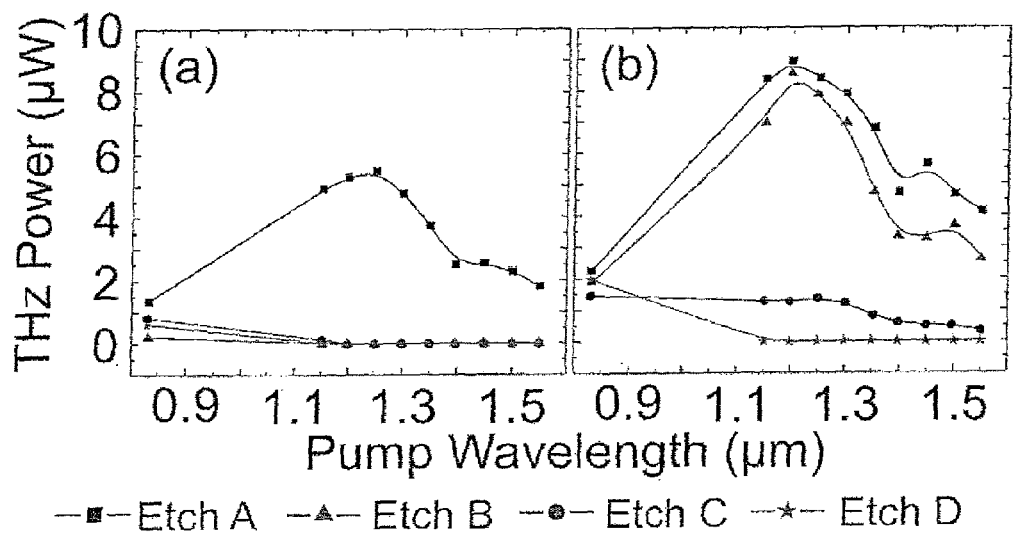
FIG. 3 shows the results of bolometric measurements of (a) NQS 2208 and (b) NQS 2213 (antennas embodying the invention) at etch depths A-D, corresponding to Fe-doped layer thicknesses of ~0.9 µm, ~0.7 µm, ~0.4 µm, and 0.0 µm.
Figure 4:
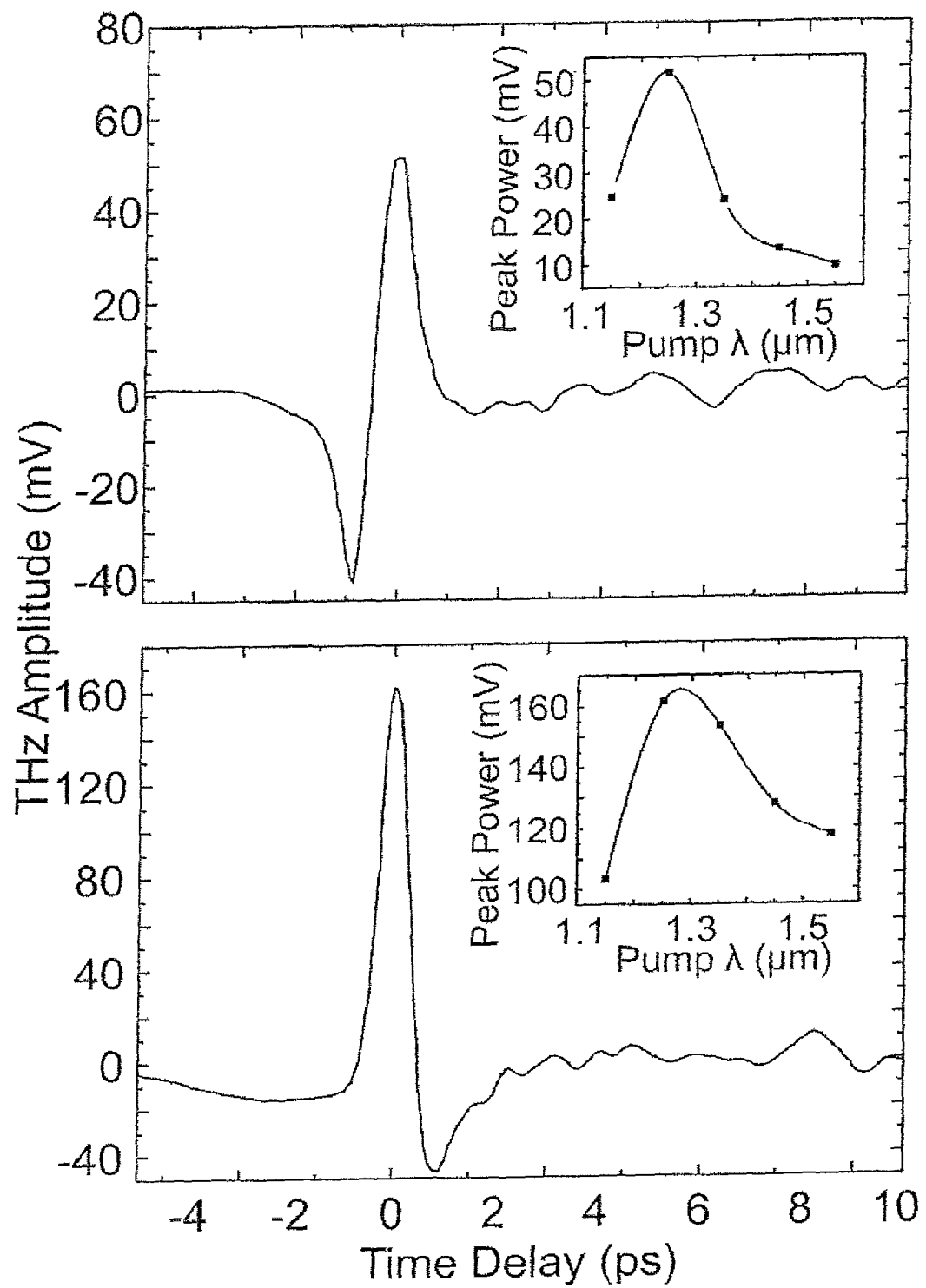
FIG. 4 shows graphs of the time domain pulse shapes for (a) NQS 2208A and (b) NQS 2213A (i.e. for embodiments of the invention) with inserts showing the peak THz signal as a function of pump wavelength.
Figure 5:
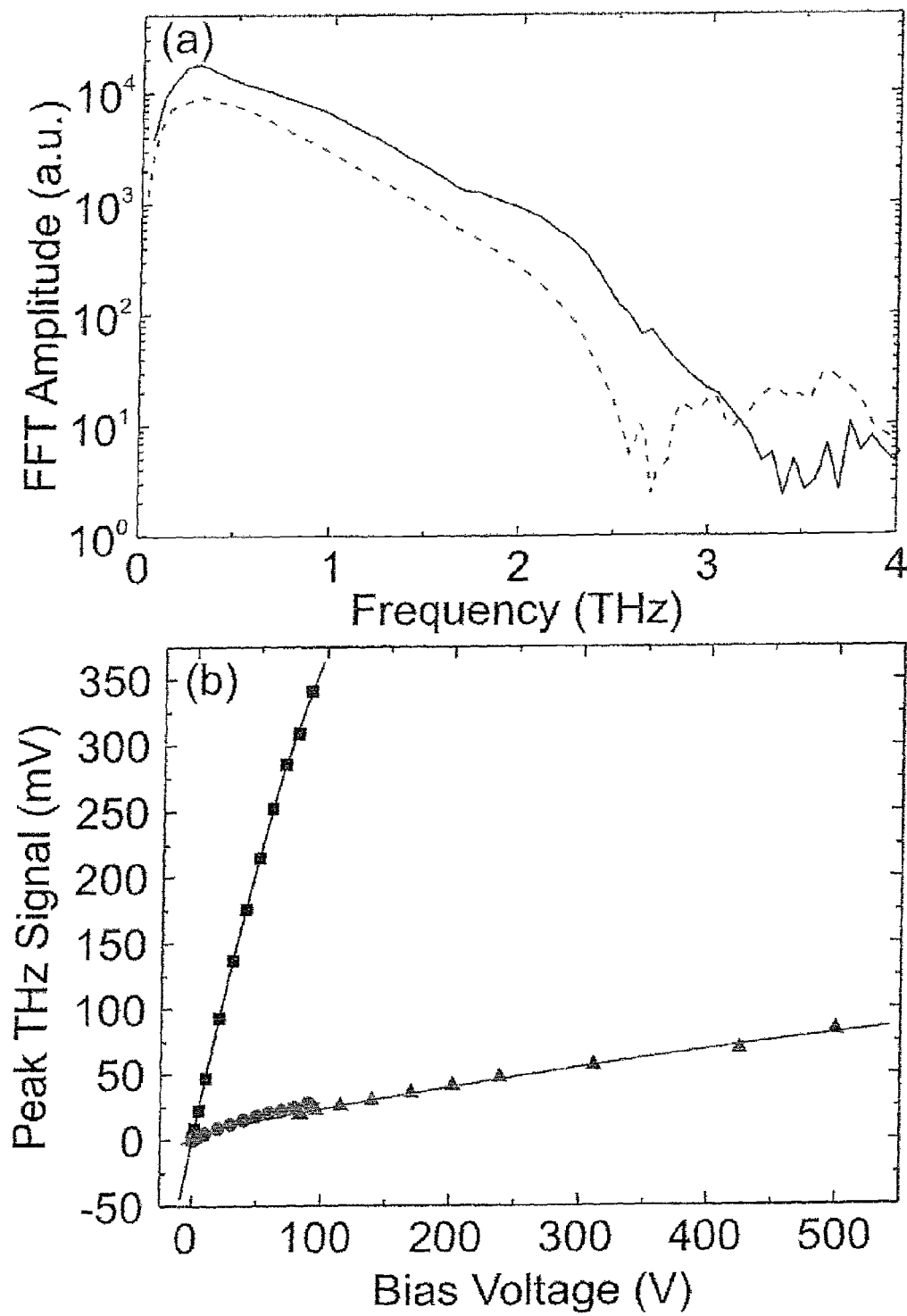
FIG. 5(a) shows a fast Fourier Transform of the NQS 2213 THz time domain pulse (dashed) (i.e. for an embodiment of the invention) compared with equivalent data for a SI-GaAs antenna (solid), and (b) comparisons of the peak THz signal obtained from NQS 2208 (circles), NQS 2213 (squares) and SI-GaAs (triangles) antennas as a function of bias voltage.

Two further wafer structures were then measured; NQS 2208, a copy of NQS 1940 to assess growth reproducibility, and NQS 2213 which contained 10% of the iron content of both NQS 2208 and NQS 1940. The results in FIG. 2 show comparable performance between NQS 1940 and its replica, NQS 2208, demonstrating the accurate growth control achieved by incorporating Fe during MOCVD growth of the wafers. Also apparent is that reducing the Fe content improves the device power output significantly. This may in part be caused by a reduction in surface roughness noticed in the antenna gap (implying fewer defects), or alternatively by a reduction in the screening of the induced electric field by the presence of excess Fe. The bandwidth of the pulse generated from each antenna was virtually identical (~2.5 THz), suggesting that lower Fe content does not increase the carrier lifetime, by reducing the number of deep acceptor states for example.

In order to assess the effect of Fe-doped InGaAs layer thickness on THz output power, and to verify that it was responsible for the THz power measured, four antennas from each of the NQS 2208 and 2213 wafers were fabricated and chemically etched through the InP capping layer and the subsequent n-type InGaAs layer (Table I below) to leave Fe:InGaAs layer thicknesses of ~0.9 µm, ~0.7 µm, ~0.4 µm, and 0.0 µm, labelled antenna A-D respectively for each wafer.

TABLE I

Layer structure and thicknesses for materials NQS 2208 and NQS 2213, where NQS 2213 has ~10% Fe doping in the Fe:InGaAs layer than NQS 2208.

| Layer Material | Layer thickness (µm) |
|---|---|
| n-InP (capping) | 0.2 |
| n-InGaAs | 0.3 |
| Fe:InGaAs | 1.0 |
| SI-InP | 0.3 |
| InP (substrate) | 500 |

Etch depth D corresponds to removal of all Fe:InGaAs from the antenna structure to reveal semi- insulating (SI) InP at a thickness of 200 µm in the antenna gap. The results in FIG. 3(a) and FIG. 3(b) show the data obtained for NQS 2208 and 2213 respectively at all four etch depths, and demonstrate significant reductions in performance as the Fe:InGaAs layer thickness is reduced. Zero output power is observed at long wavelength pumps for both wafer structures below etch depth D, and etch depths B and C demonstrate reduced or zero performance for wafer NQS 2213 and 2208 respectively. All etch depths on each wafer produce a THz signal at 830 nm pump, presumably due to emission from the SI-InP layer beneath the Fe:InGaAs layer.

The best performing antenna from each material (both at etch depth A) were measured in a full TDS system using the tuneable OPO output for the pump beam, and the Ti:Sapphire laser as the probe beam as shown in FIG. 1(b). The probe wavelength was kept at a constant 830 nm to negate variations in detection efficiency which could arise by using equivalent pump and probe wavelengths from the OPO for each measurement. Time-resolved images of the pulses obtained for each wafer at 1250 nm pump are shown in FIGS. 4(a) and 4(b), with inserts showing a similar trend in maximum output signal as a function of pump wavelength as observed in the previous bolometer measurements. A Fast Fourier Transform (FFT) of the 1250 nm signal for wafer NQS 2213 is provided in FIG. 5(a) and compared to a signal obtained from a semi-insulating GaAs (SI-GaAs) antenna at 800 nm pump/probe. The Fe:InGaAs antenna demonstrates a signal to noise in excess of 1000:1, and a bandwidth of 2.5 THz, approximately 800 GHz lower than the SI-GaAs antenna. This reduced bandwidth is attributed to the increased pump pulsewidth from the OPO (~200 fs) when compared with the 100 fs pulsewidth from the 800 nm source used to measure the SI-GaAs antenna. FIG. 5(b) shows comparisons of the peak THz signal measured as a function of wavelength for the NQS 2208 and 2213 wafers compared with a standard SI-GaAs wafer, measured at 100 V bias and 100 mW pump power. The NQS 2213 antenna (with lower Fe doping) demonstrates significantly higher output power at lower bias voltages than either of the other samples, indicating that even lower Fe doping levels may be usefully investigated in future work.

Thus, the inventors have demonstrated that Fe doping introduced during MOCVD of InGaAs and InGaAsP can form photoconductive material capable of generating terahertz radiation across a wide range of wavelengths, with high levels of reproducibility and control. Furthermore, we find that increased levels of Fe doping can have a detrimental effect on device output power, probably owing to an increased induced defect density within the materials at higher doping densities. The bandwidth achieved from these photoconductive emitters was of order 2.5 THz, primarily limited by the pulsewidth of the OPO laser used for carrier generation, with a measured SNR of ~1000:1. The output powers demonstrated were larger in both materials systems than equivalent SI:GaAs antennas made with identical geometry. Our work shows that MOCVD growth of InGaAs and InGaAsP-based materials with Fe-doping incorporated during growth could be useful in the construction of portable, lower cost THz spectroscopy systems based on 1.55 µm laser emission.

Thus, terahertz emission from Fe-InGaAs and Fe-InGaAsP grown using MOCVD with epitaxially-incorporated Fe has been demonstrated with certain embodiments.

The generation of pulsed THz radiation from Fe:InGaAs and Fe:InGaAsP, both made using MOCVD with epitaxially incorporated Fe, has been shown, using pump wavelengths between 800 nm and 1.55 µm. The growth technique allowed precise control over the Fe doping level. The terahertz emission from each wafer showed bandwidths in excess of 2.5 THz, with signal-to-noise ratios in excess of 1000:1. The THz output powers were found to be strongly dependent on the iron content, the thickness of the semi-insulating Fe:InGaAs layer, and the excitation wavelength used.

Figure 6:
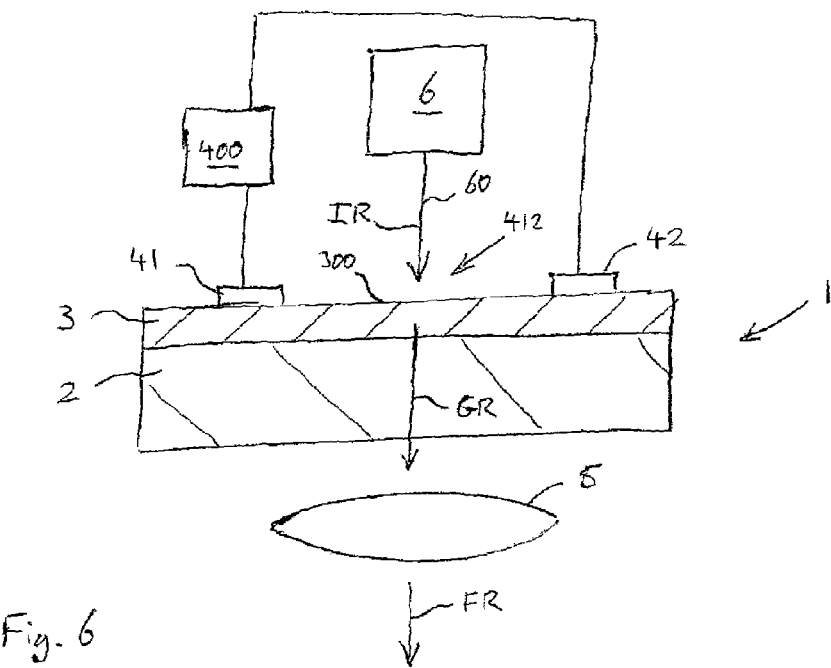
FIG. 6 is a schematic illustration of radiation generating apparatus embodying the invention.

Referring now to FIG. 6, this is a schematic representation of radiation generating apparatus embodying the invention. The apparatus comprises an antenna 1 which includes a substrate 2 supporting a layer of grown, doped semiconductive material 3. The semiconductive material may, for example, be InGaAs, InGaAsP, InGaAlAs, or other suitable material, doped with a dopant. The dopant may, for example, be an element, a transition metal element, chromium, vanadium, or iron. In the figure, the doped semiconductive layer 3 is shown to be arranged directly on the substrate 2. However, in alternative embodiments there may be one or more intermediate layers between the substrate and doped semiconductive layer. An illumination source 6 is arranged to direct illuminating radiation 60 at a portion 300 of an upper surface of the doped semiconductive layer 3, generally at a gap 412 between two electrodes 41, 42 spaced apart on the upper surface. The illumination source 6 is arranged such that the illuminating radiation 60 has photon energies sufficient to excite electron-hole pairs in the doped semiconductive material layer 3 (in other words the photon energies at least equal the band gap of the doped semiconductive material). These electrons and holes are accelerated by means of a voltage or potential difference applied between the electrodes 41, 42 by a voltage source 400. The acceleration of the electrons and holes generates radiation, and this generated radiation from the doped semiconductive layer is transmitted through the substrate, emerging on a reverse side of the antenna, where it is then focused by a lens 5 to produce focused radiation FR.

Figure 7:
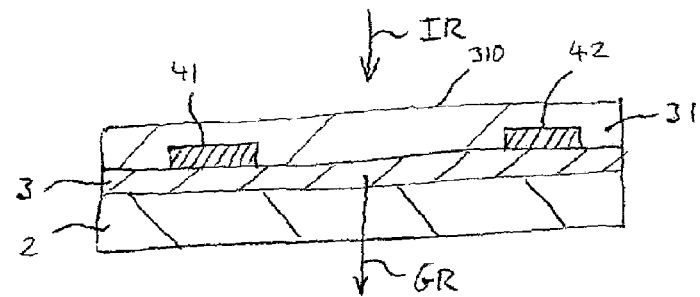
FIG. 7 is a schematic illustration of an antenna embodying the invention and being used to generate radiation.

Referring now to FIG. 7, this illustrates an alternative form of antenna embodying the invention. Here, a layer 3 of grown, doped semiconductive material is again supported on a substrate 2. First and second electrodes 41, 42 have been formed on the layer 3, and an encapsulating layer 31 has been formed over the electrodes. This encapsulating layer is formed from material that is at least substantially transparent to the illuminating radiation IR, which is incident on an upper surface 310 of the encapsulating layer. Thus, the incident radiation is able to penetrate the antenna and reach the layer 3, in which it can produce electron-hole pairs. A bias is applied between the first and second electrodes 41, 42 by means not shown in the figure, and this accelerates the generated electron-hole pairs to generate THz radiation GR which again passes through the substrate 2.

Figure 8:
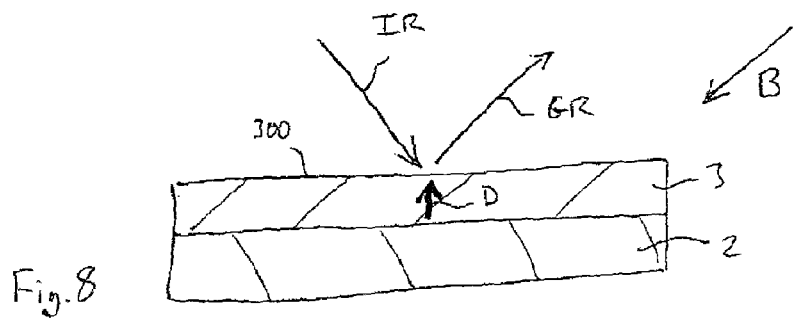
FIG. 8 illustrates the generation of THz radiation in another embodiment of the invention.

FIG. 8 illustrates an alternative method of generating THz radiation in an embodiment of the invention. Here, a layer 3 of grown, doped semiconductive material is supported on a substrate 2. Incident radiation IR having photon energies at least equal to the band gap of the grown, doped semiconductive material is directed at an upper surface 300 of the structure, in a direction having components both normal to and parallel to the surface 300. THz dipoles D are generated in the bulk material 3, and these THz dipoles generate THz radiation GR by known mechanisms. This generated radiation GR is emitted generally from the surface 300 of the structure, in a direction which also has components normal to and parallel to the surface 300. The generation of THz radiation in this example is increased by the application of a magnetic field B to the structure. The magnitude and direction of the applied magnetic field may be adjusted using known techniques to optimise the emission of THz radiation.

Figure 9:
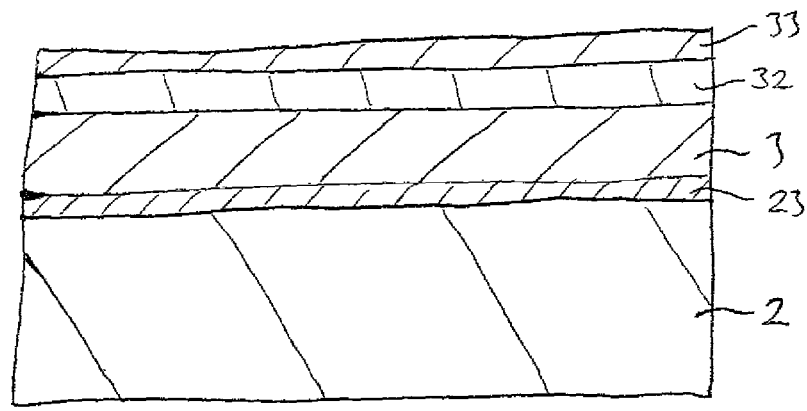
FIG. 9 illustrates a multilayer structure for use in embodiments of the invention.

Referring now to FIG. 9, this is a schematic representation of a multi-layer structure manufactured as part of a process for manufacturing a photo conductive antenna embodying the invention. The multilayer structure comprises an InP substrate of thickness 500 microns. A layer 23 of SI-InP of thickness 0.3 microns has been formed (e.g. grown) on the substrate 2. Next, a layer of FE-doped InGaAs 3 of thickness 1.0 microns has been grown on the layer 23. Then, a layer 32 of n-InGaAs of thickness 0.3 microns has been formed (e.g. grown) on the grown, doped semiconductive layer 3. Finally, a capping layer 33 of thickness 0.2 microns, of n-InP has been formed on layer 32. To produce antennas embodying the invention, the layers 33 and 32 may be patterned, at least partially removed, and electrical contacts may be made to them using techniques known in the art. For example, electrodes for applying bias voltages may be formed directly on the layer 3, after removal of portions of layers 32 and 33, or alternatively the electrodes may be formed on areas of layer 32, after suitable removal of portions of layer 33 etc.

Figure 10:
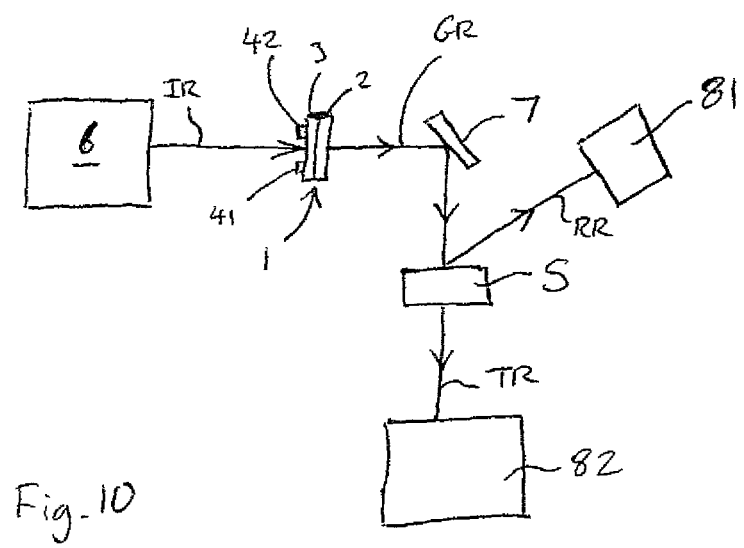
FIG. 10 is a schematic illustration of spectroscopy apparatus embodying the invention.

Referring now to FIG. 10, this is a highly schematic representation of spectroscopy apparatus embodying the invention. The apparatus comprises a photoconductive antenna 1, itself comprising a substrate 2 supporting a grown, doped layer of semiconductive material 3. First and second electrodes 41 and 42 are formed on this layer 3, and incident radiation of the appropriate wavelength, from an illumination source 6, is directed at a gap between the electrodes so as to generate electron-hole pairs in the layer of material 3. A bias voltage is applied between the electrodes 41 and 42 to accelerate the generated carriers, so generating THz radiation. This generated radiation GR is transmitted through the structure 1 and is directed by directing means (in this example simply comprising a reflector or mirror 7) at a sample S. Some of this generated radiation is transmitted through the sample S, and the transmitted radiation is detected by an appropriately arranged detector 82. In this particular example a portion of the generated radiation is reflected from the sample, and this reflected radiation RR is detected by a further detector 81. It will be appreciated that in alternative embodiments just the transmitted radiation, or indeed just the reflected radiation may be detected. It will be appreciated that the spectrum of transmitted radiation detected by detector 82 will be indicative of THz absorption characteristics of the sample S.

Figure 11:
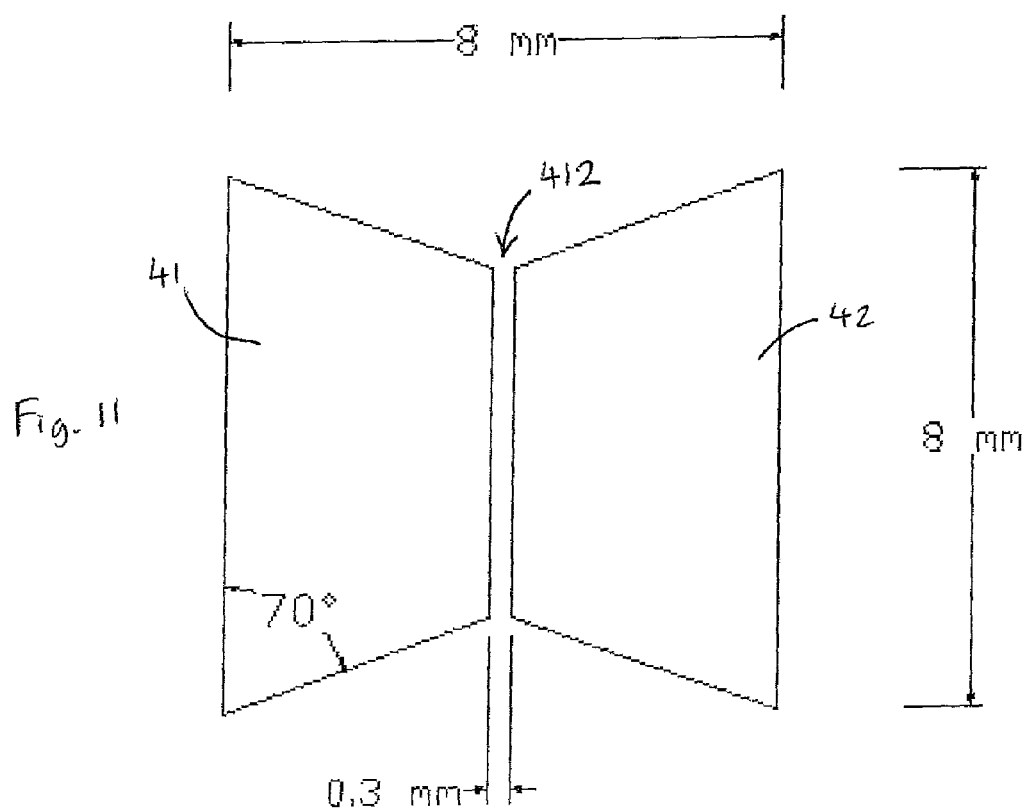
FIG. 11 shows an electrode arrangement used in an antenna embodying the invention.

Referring now to FIG. 11, this illustrates an electrode pattern which may be employed in embodiments of the invention. For example, metal electrodes (such as gold electrodes) having the illustrated shape may be formed on the surface of a layer of grown, doped semiconductive material. Radiation comprising photons of the appropriate frequencies may then be directed at the gap 412 defined between the electrodes. Application of a bias potential between the electrodes can then accelerate carriers excited by the illuminating radiation so as to generate THz radiation. The electrode pattern shown in FIG. 11 can generally be described as a bow-tie configuration, and in this example the gap width is approximately 0.3 mm.

It will be appreciated that, whilst certain embodiments incorporate an FE-doped layer, where the FE is incorporated in the growth of the layer, other dopants may be used in alternative embodiments, those dopants giving rise to mid-band states in the semiconductive layers so as to provide electron and/or hole traps. These other dopants can also result in effective THz generation when those dopants are incorporated in a layer of InGaAs, InGaAsP or InGaAlAs during the growth of the layer. Such dopants are typically transition metal elements, e.g. chromium or vanadium.

It will also be appreciated that a variety of growth techniques may be used for growing the doped semiconductive layers in embodiments of the invention. These techniques include MOCVD, LPE, and MBE.

In certain embodiments, fabrication of antennas may comprise growing a wafer comprising a grown, FE-doped layer supported on a substrate. The technique may further comprise the formation (for example growth) of an N-doped layer of InGaAs over the FE-doped layer, patterning of that InGaAs layer to define contact regions, and then formation of metal contacts on those contact regions. These metal contacts may, for example, define electrodes for applying bias voltages or for measuring generated voltages or currents.

Referring now to FIGS. 12 to 17, the following description demonstrates the efficient generation of terahertz (THz) radiation from Fe-doped InGaAs-based photoconductive antennas. Time-domain data is presented showing generation of pulsed THz radiation from antennas fabricated on two different wafers, optimized to maximize the near infrared-to-THz conversion efficiency. Detection was performed using both (110) ZnTe and GaP crystals, with pump and probe wavelengths being adjusted from 800 nm to 1550 nm using a cavity-tuned OPO pumped by a pulsed near-infrared Ti:Sapphire laser.

As discussed above, Terahertz frequency (THz) radiation is now widely used as a tool for non-destructive spectroscopy of a variety of materials, as well as for imaging and the studies of condensed matter systems. This has driven the desire to design cheap, compact THz systems, and move away from the Ti:Sapphire laser technology which has been predominantly used to date.

Recent refinements in alternative, compact pulsed laser sources for communications, such as Er-doped fibre lasers operating at 1550 nm, may be incorporated in embodiments of the invention to provide efficient THz emitters operating in this pump wavelength range, and provide portable THz spectrometers.

In the following description, we demonstrate THz generation from InGaAs-based photoconductive emitters pumped with wavelengths ranging from 830 nm to 1550 nm, with single crystals of either 1 mm thick ZnTe, or 150 µm thick GaP being used for coherent detection. The apparatus (FIG. 12) consists of a 72 MHz, 120 fs, 830 nm Ti:Sapphire laser pumping a cavity tuned Optical Parametric Oscillator (OPO) containing a quasi-phase matched, periodically poled lithium niobate crystal. The idler output from the OPO, used to pump the photoconductive antennas, was tuneable from 1150 nm to 1550 nm. The apparatus was designed so that the THz radiation could be probed either at 830 nm (probe beam 1, from the Ti:Sapphire laser) or at the same wavelength as the pump beam (probe beam 2, from the OPO), using a fraction of the OPO output power. THz detection was performed using an electro-optic crystal (ZnTe, or GaP) followed by measurement on a pair of balanced photodiodes.

The Fe:In$_{0.53}$Ga$_{0.47}$As wafers were grown using metal-organic chemical vapour deposition (MOCVD) in a horizontal quartz reactor. Fe was epitaxially incorporated into the structure during growth, giving precise control over dopant levels and excellent reproducibility. Two wafers were used; NQS2208 and NQS2213 which had average Fe concentrations of $5 \times 10^{18}$ cm$^{-3}$ and $3 \times 10^{16}$ cm$^{-3}$ respectively and results are presented from photoconductive antennae made from each.

Bowtie antennas were lithographically defined on each wafer, with an electrode separation of 400 µm. Metallization was achieved using thermally evaporated gold (200 nm) preceded by a titanium adhesion layer (20 nm). The antennas were aligned in the time-domain system in transmission mode and THz radiation was collimated onto the first parabolic mirror using a hyper-hemispherical silicon lens fixed to the back of each device. The electrode gap was asymmetrically illuminated by focussing the pump beam close to the anode to provide maximum THz intensity.

Our results will now be discussed. All experiments were performed using a 50 V bias applied to the emitter electrodes, electrically chopped at 10 kHz, with 50 mW pump power incident on the antennas. The THz path and OPO cavity were purged with ultra-dry nitrogen gas to remove water absorption. Initial tests were performed using a ZnTe crystal for electro-optic sampling. Experiments involving 800 nm for both excitation and detection were performed using a separate, 100 fs pulsewidth Ti:Sapphire laser.

Figure 13:
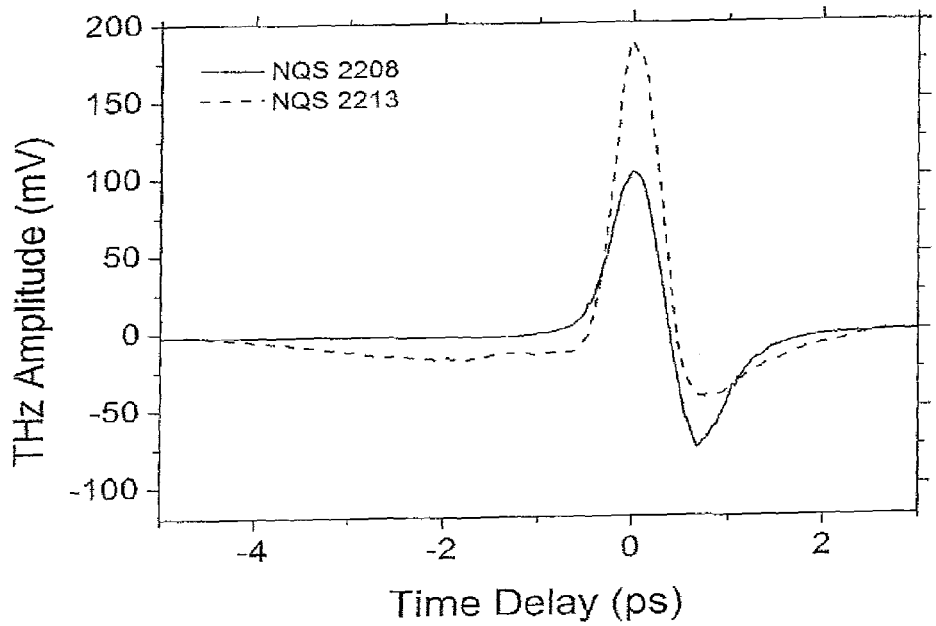
FIG. 13 shows the time domain pulses obtained from antennas embodying the invention, formed on NQS2208 and NQS2213 wafers, optically excited at 1550 nm, and probed at 830 nm.
Figure 14:
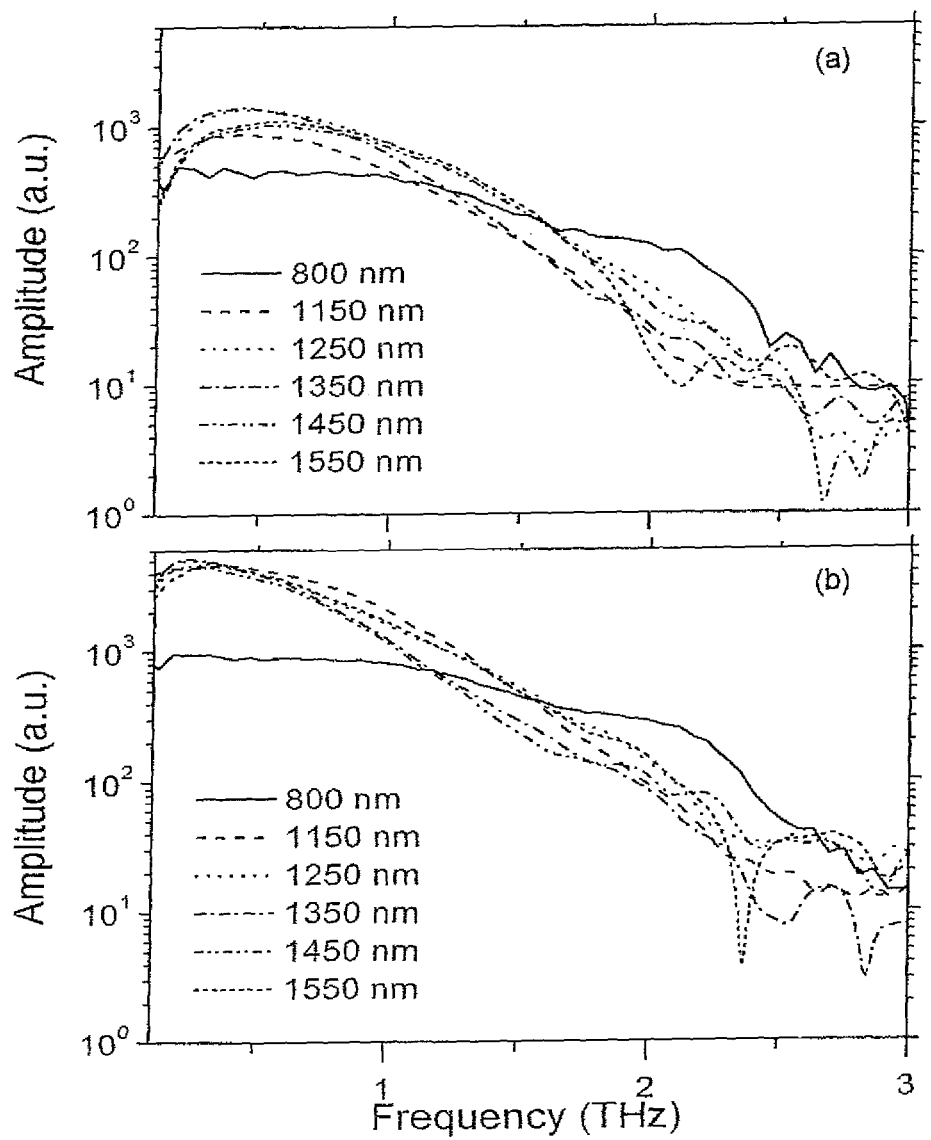
FIG. 14 shows frequency spectra obtained by Fourier transform of emission pulses generated using Fe doped InGaAs photoconductive emitters embodying the invention on (a) NQS2208 and (b) NQS2213 when excited by varying wavelength pump beams (detection was with an 830 nm probe beam on a ZnTe crystal)

FIG. 13 shows the time domain signals obtained from each antenna, excited with 1550 nm pulses and detected at 830 nm. The second wafer, NQS2213, demonstrates a significant (~80%) increase in THz power compared with NQS2208. This is owing to an improvement in surface quality of the wafer as the Fe concentration is reduced, which reduces the formation of InFe precipitates and allows easier fabrication and greater surface uniformity in the antenna gap. FIG. 14 however, shows that both antennas demonstrate comparable bandwidths as the excitation wavelength is varied, implying that the reduction in Fe concentration does not increase carrier lifetime by removing deep acceptor states.

A reduction in bandwidth is evident for both antennas as the pump laser wavelength is increased from 800 nm to 1550 nm—a direct result of the increase in laser pulsewidth (~100 fs to ~180 fs respectively).

Figure 12:
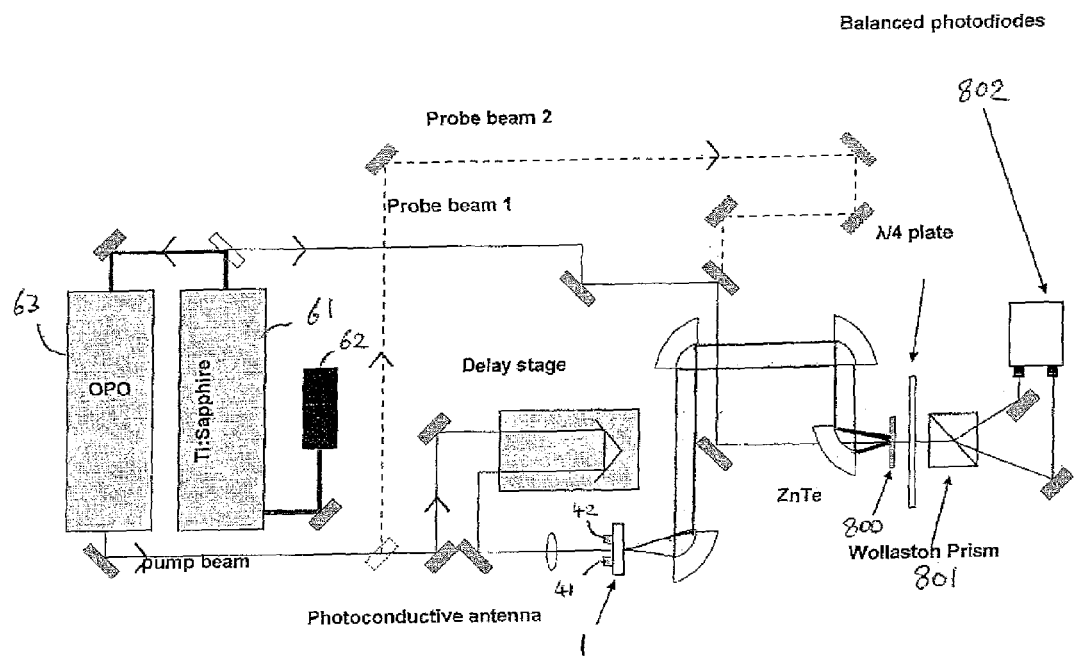
FIG. 12 shows the THz time domain system used in further embodiments of the invention (Probe beams 1 and 2 represent the 830 nm and tuneable OPO beams respectively)
Figure 15:
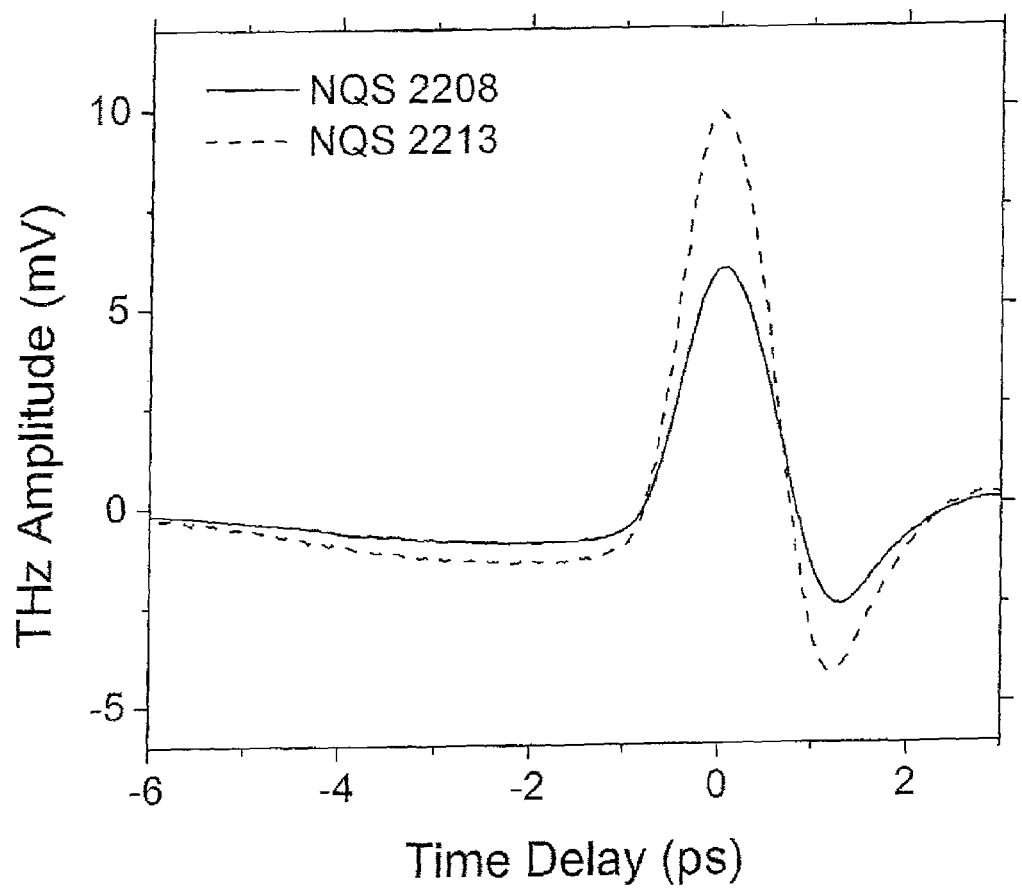
FIG. 15 shows time domain pulses obtained from antennas embodying the invention and formed on NQS2208 and NQS2213 wafers, optically excited and detected (on ZnTe) using 1550 nm wavelength pulses.

In order test the viability of the system for use with a fibre laser for both pump and probe beams, the system was slightly altered to allow detection of the THz signal using a fraction of the OPO output signal (~5 mW per photodiode, probe beam 2 in FIG. 12). FIG. 15 shows the time domain pulses obtained using a wavelength of 1550 nm for both pump and probe beams. Again, wafer NQS2213 (which has a lower Fe concentration) demonstrates significantly more power than the identical antenna formed on NQS2208.

Figure 16:
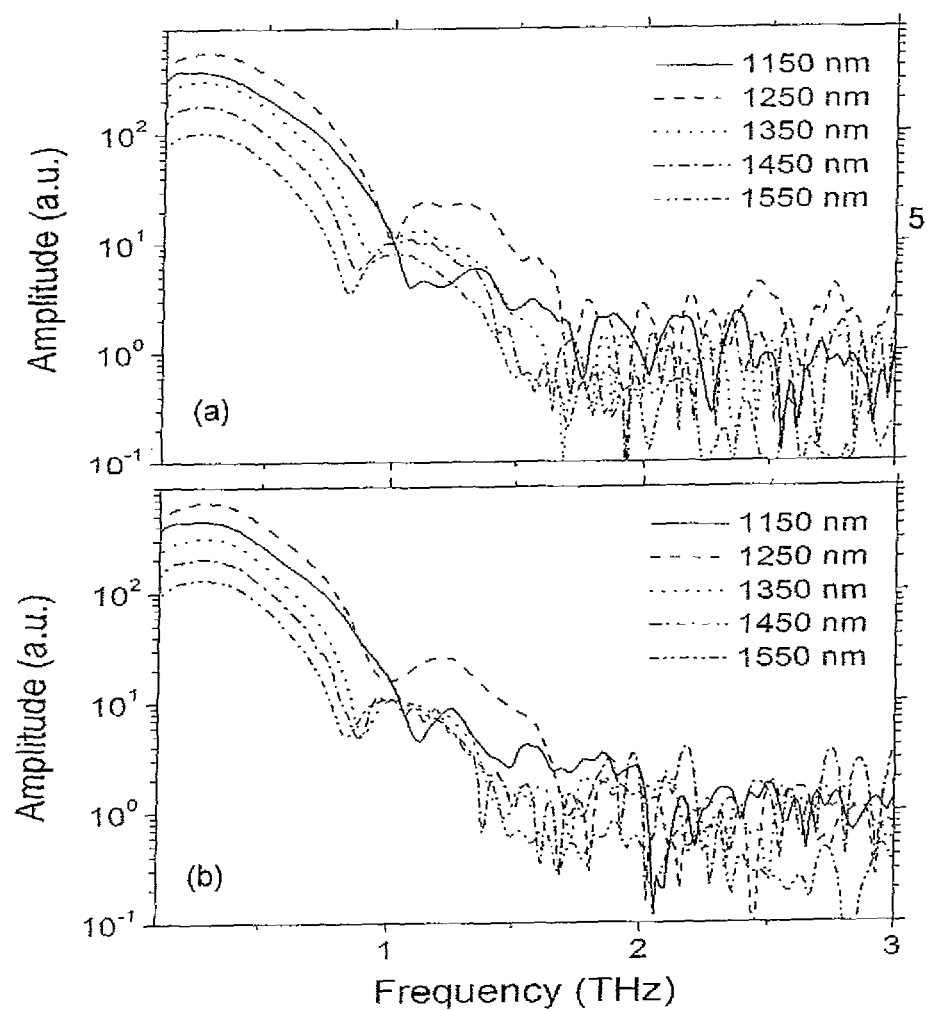
FIG. 16 shows frequency spectra obtained by Fourier transform of emission pulses generated using Fe doped InGaAs photoconductive emitters (embodying the invention) on (a) NQS2208 and (b) NQS2213 when excited and probed using coherent long wavelength (1150-1550 nm) pulses.
Figure 17:
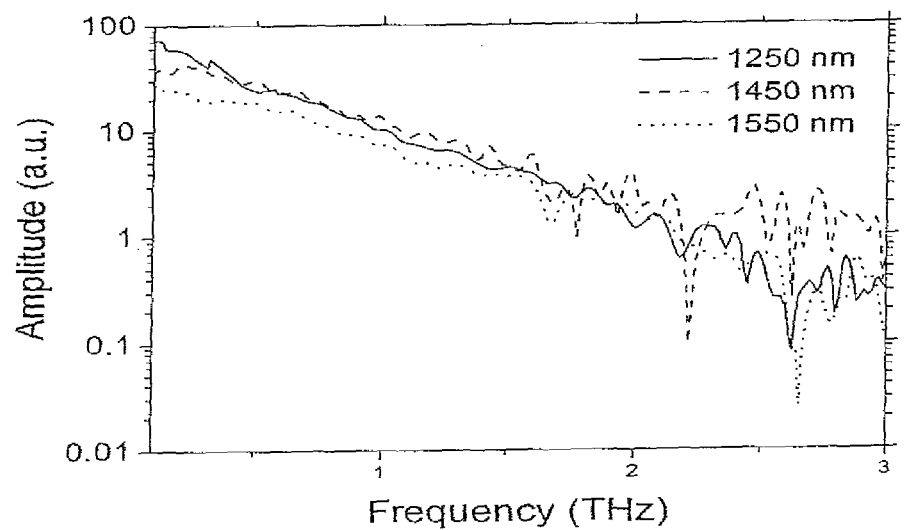
FIG. 17 shows fourier transforms of ultra-fast time domain pulses generated from NQS2213 at three wavelengths; 1250 nm, 1450 nm and 1550 nm, electro-optically detected using equivalent wavelength probe pulses on a GaP detector.

FIG. 16 shows Fourier transforms of the time domain data obtained using pump and probe wavelengths ranging from 1150 nm to 1550 nm. The bandwidth decrease from ~2.5 THz to ~1.5 THz is directly attributed to the increased pulsewidth of the probe beam from 120 fs (Ti:Sapphire output) to ~180 fs (OPO output). The Fourier transforms also reveal an absorption in the frequency domain which appears to redshift as the detection wavelength is increased. This may be attributed to the ZnTe detection crystal under long wavelength excitation since the artefact is not present when using 830 nm detection. This is supported by FIG. 17, which shows equivalent measurements performed at three wavelengths (1250 nm, 1450 nm and 1550 nm), but using a 150 µm thick, single crystal GaP electro-optic detector. The reduction in signal-to-noise ratio and relative intensities of each frequency component (also observed as a large reduction in THz signal strength in the time domain) arise from the short interaction length of the THz radiation and probe beam within the GaP crystal, and are likely to increase to comparable values to those obtained with ZnTe should a thicker detector crystal be used. The thinner GaP detector crystal, though, results in an increase in bandwidth (to ~2 THz) owing to a reduction in attenuation of higher frequency components in the thin crystal when compared to the thicker ZnTe. Of primary importance however, is that the transient absorption observed when using the ZnTe crystal is no longer present.

Thus, we have demonstrated the use of epitaxially grown Fe doped InGaAs for fabricating THz photoconductive emitters that can be excited at wavelengths ranging from 800 nm (the traditional, Ti:Sapphire operating wavelength) up to communications wavelengths (1550 nm). These may be used as the basis of a portable, fibre-laser based, THz-TDS system, embodying the invention, which have wide scale applicability beyond the research laboratory environment. Furthermore, we have shown that control of the Fe doping level allows tailoring of the THz signal strength, and have demonstrated the use of both ZnTe and GaP as THz detectors with long wavelength probe beams.

Figure 18:
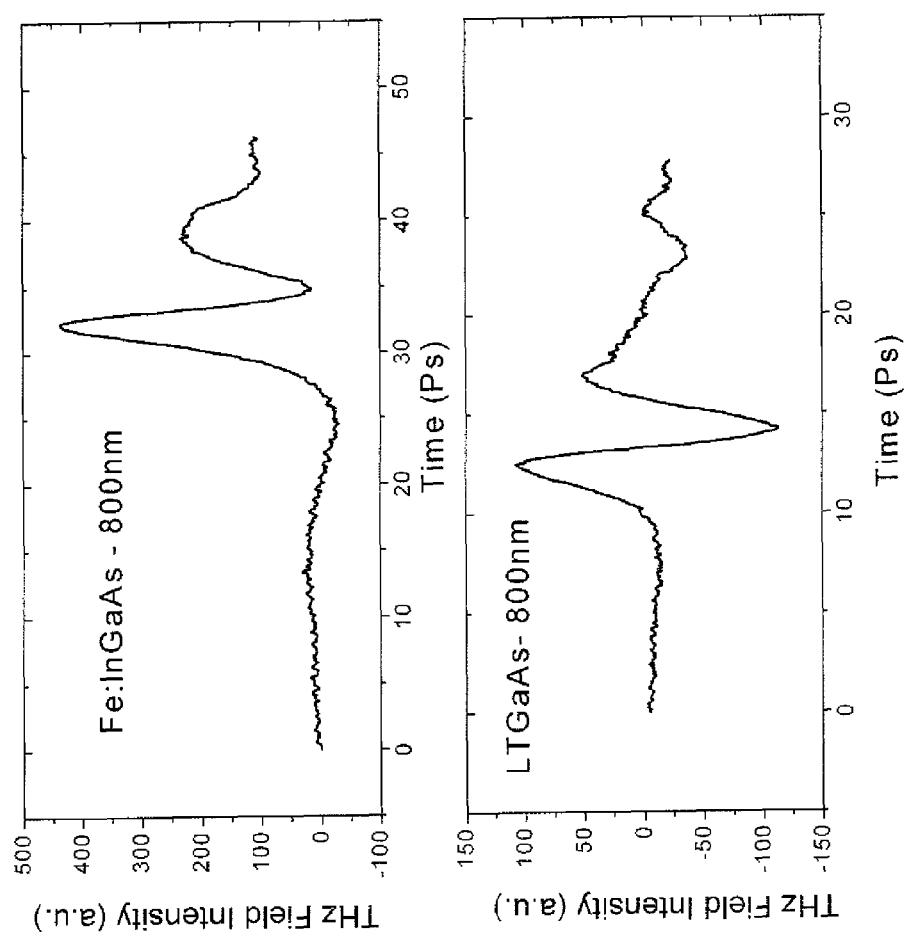
FIG. 18 shows a comparison of detection results between a low-temperature grown GaAs structure and a Fe:InGaAs structure (detector) embodying the invention.
Figure 19:
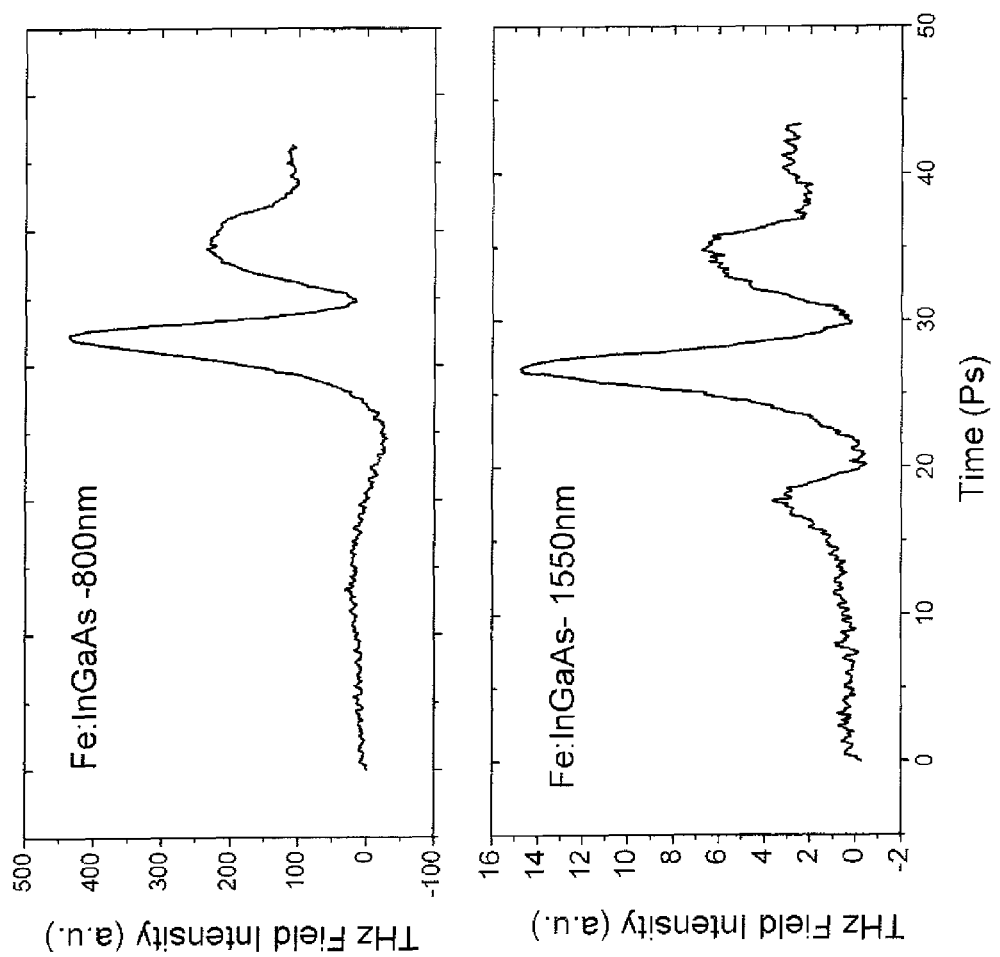
FIG. 19 shows a comparison of Fe:InGaAs detector results using different probe beams.
Figure 20:
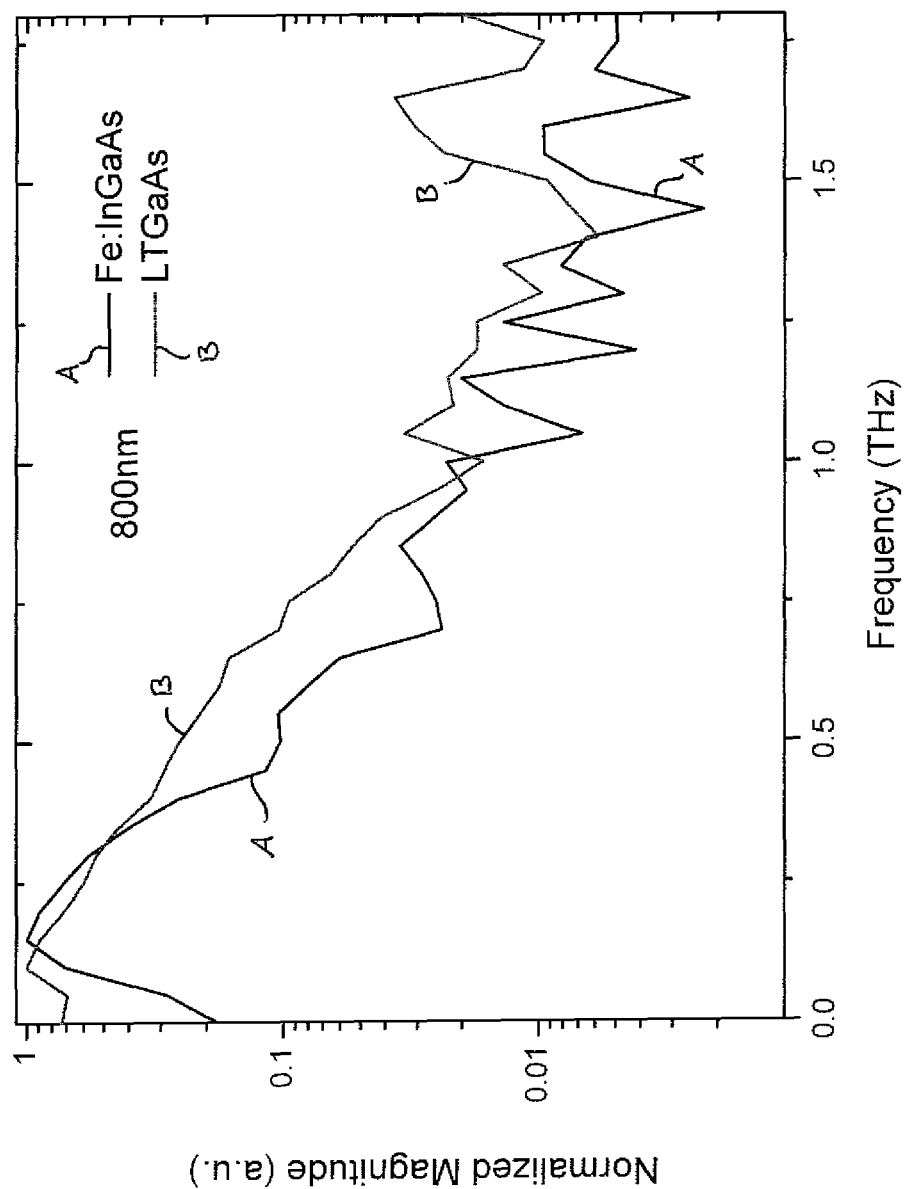
FIGS. 20 and 21 show Fourier transforms of the data shown in FIGS. 18 and 19 respectively.
Figure 21:
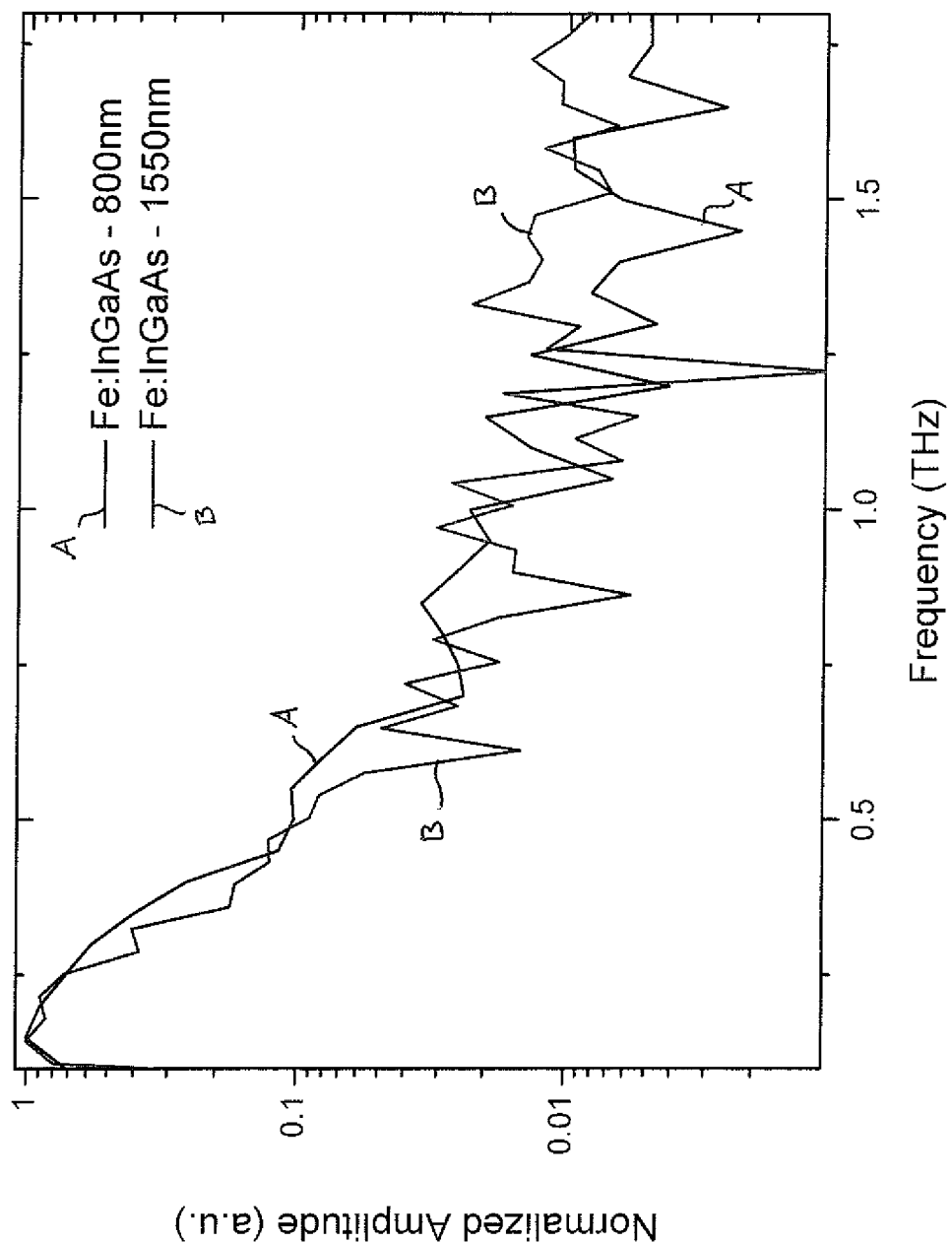

Referring now to FIGS. 18-21, the present inventors have demonstrated the use of Fe:InGaAs as a detector (photoconductive detector), using both an 800 nm and a 1550 nm probe beam. FIG. 18 is a comparison of detection with an 800 nm probe wavelength using Low-temperature (LT) grown GaAs, and Fe:InGaAs. The vertical scale is in 'arbitrary units', and it will be noted that similar signal-to-noise ratios are seen. FIG. 19 is a comparison of Fe:InGaAs detectors (each embodying the invention) using an 800 nm and a 1550 nm probe beam. FIGS. 20 and 21 are Fourier transforms of the data shown in FIGS. 18 and 19. It will be noted that the bandwidth is, almost certainly, limited by the laser pulse width, and could be improved with a dedicated short-pulse near-infrared laser. It is notable that far lower probe power levels are required for photoconductive detection with Fe:InGaAs, than with LT-GaAs. The inventors have determined that, when using Fe:InGaAs as a photoconductive detector, about 3 mW is required for the probe beam at either 800 nm or 1550 nm. In fact, even 1 mW gives a good signal. In contrast, when using low-temperature GaAs at with an 800 nm probe beam, one typically requires 50 mW probe power. The use of lower powers is clearly advantageous. For example, the use of a much lower power for the Fe:InGaAs photoconductive detectors is clearly very beneficial for applications of THz systems, since it means that one can use lower-power near-infrared laser sources. The inventors have also also found that, in certain embodiments, using higher probe powers in Fe:InGaAs leads to a reduction in detected signal, owing to the resulting large photocurrents.

Further embodiments will now be described. To verify that the Fe:InGaAs layer was responsible for the generation of THz radiation, and to assess the effect of Fe:InGaAs layer thickness on the generated THz power, three emitters were prepared from each of two wafers—wafer $2208_{100}$ and wafer $2213_{0.8}$—and measured using bolometric detection. These two wafers had iron concentrations of $5 \times 10^{18}$ cm$^{-3}$ and $4 \times 10^{16}$ cm$^{-3}$, respectively, and sheet resistivities (measured in the dark) of $R_{sh} = 4.0 \times 10^4$ and $6.2 \times 10^6$ Ohm/sq. The subscript assigned to each wafer number refers to the percentage of Fe dopant with respect to the highest doped wafer, wafer 2208. The surface of the higher Fe-doped material, $2208_{100}$, was observed to be significantly rougher than $2213_{0.8}$, owing to the formation of FeAs precipitates during growth. The wafers were chemically etched between the electrodes to leave Fe:InGaAs material with thicknesses of 0.9 micro m, 0.4 micro m, and 0.0 micro m (samples labelled A-C, respectively). Etch depth C, therefore, revealed the 300 nm epitaxially-grown SI:InP buffer layer in the electrode gap. The results demonstrated THz emission over the complete pump wavelength range, with optimum performance achieved at around 1250 nm. A slight dip in measured power observed at 1450 nm was caused by a reduction in the OPO pump beam quality (observed as increased laser noise and pulsewidth) at this wavelength. The THz power followed the same trend for both wafers, although $2213_{0.8}$ emitted higher power than $2208_{100}$. Each wafer demonstrated a significant reduction in THz emission as the Fe:InGaAs layer thickness was reduced. No output power was observed for >830 nm wavelength excitation from either wafer at etch depths exceeding 0.6 micro m, (B) although a THz signal was obtained from all emitters at 830 nm excitation, a result of emission from the underlying SI-InP layer. The emitters which produced the highest output power from each material (etch depth A) were measured in the THz-TDS system of FIG. 1 using 830 nm detection. The resulting frequency spectra for excitation wavelengths from 1150 nm to 1550 nm were obtained, as were time-domain pulse shapes for each emitter at 1550 nm excitation. Across the full pump wavelength range, the emitters each exhibited bandwidths of >2 THz before the signal entered the noise floor. This bandwidth is limited by the pulsewidth of the OPO laser excitation, measured (using autocorrelation) to be >200 fs. The system was then modified to allow excitation and detection of the THz signal using long (1150-1550 nm) wavelengths. Initially, the same ZnTe crystal was used for detection. Fast Fourier transforms of the frequency-domain signals obtained from the emitter formed on wafer $2213_{0.8}$ showed a reduction in bandwidth to approximately 1.5 THz, alongside a strong spectral feature which redshifts with increasing pump/probe wavelength. This is thought to arise from a mismatch in the phase velocity of the THz signal and the group velocity of the probe laser pulse, causing destructive interference within the thick ZnTe crystal, which was subsequently replaced with a thinner, 150-micro m-thick GaP crystal. The results from the GaP crystal showed that the transient feature observed with ZnTe was no longer present, and the bandwidth was restored to approximately 2.0 THz, slightly less than that observed using 830 nm detection owing to the increased probe pulsewidth. The poorer signal quality observed using GaP detection arises from the reduced crystal thickness, resulting in a lower interaction length between the THz signal and probe pulse within the detector crystal.

Figure 22:
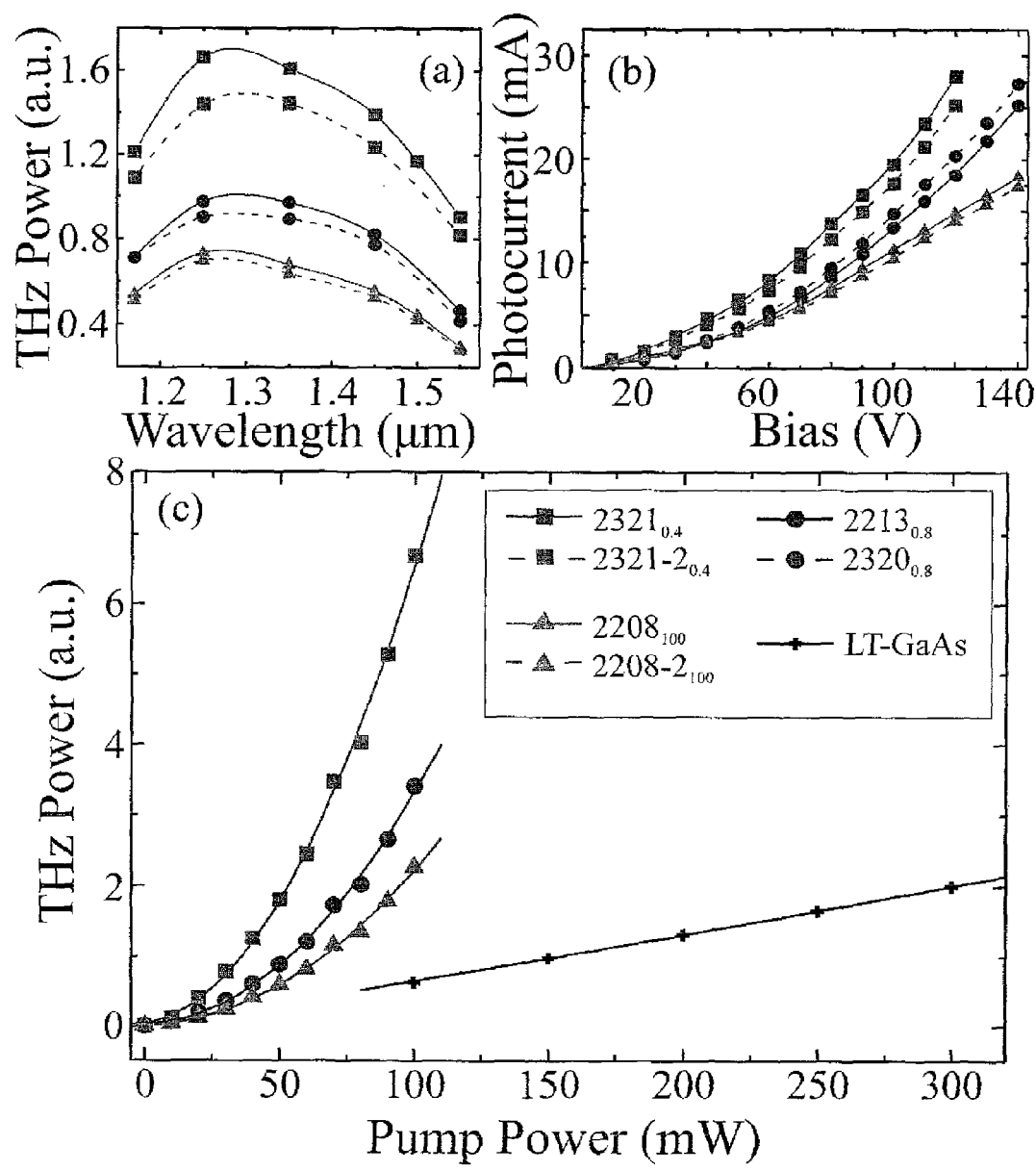
FIG. 22 shows results of measurements performed on certain embodiments of the invention.

Referring now to FIG. 22, to investigate further the effect of Fe concentration, new wafers were fabricated as follows: $2208_{100}$-2 (a repeat fabrication of $2208_{100}$, Fe doping $5 \times 10^{18}$ cm$^{-3}$); $2320_{0.8}$ (Fe doping $4 \times 10^{16}$ cm$^{-3}$, a repeat growth of $2213_{0.8}$); and $2321_{0.4}$ (a further Fe reduction to $2 \times 10^{16}$ cm$^{-3}$, $R_{sh} = 2.1 \times 10^7$ Ohm/sq). FIG. 22 shows: (a) THz power as a function of excitation wavelength for equivalent emitter pairs: $2321_{0.4}$ and $2321_{0.4}$-2 (squares); $2213_{0.8}$ and $2320_{0.8}$ (circles); and $2208_{100}$ and $2208_{100}$-2 (triangles); (b) Corresponding variation in photocurrent with bias voltage (1550 nm, 50 mW excitation); and (c) THz signal with excitation power, for emitters on wafers $2208_{100}$, $2213_{0.8}$, and $2321_{0.4}$ (1550 nm excitation), and an LT:GaAs emitter under 800 nm excitation. In more detail, FIG. 22(a) shows the peak THz signal measured as a function of wavelength for all wafers. The lowest doped (and correspondingly highest sheet resistivity) wafer, $2321_{0.4}$, exhibits the highest THz signal strength, most likely because of the reduced level of Fe scattering sites (and a reduction in the trapping of photoexcited carriers), while the bandwidth is unaffected (within the limitations of the measurement system) by the reduction in carrier traps. The photocurrent as a function of bias voltage (at 1550 nm, 50 mW excitation) is given in FIG. 22(b), and demonstrates the expected increase in carrier generation (observed as an increase in photocurrent) as the Fe doping is reduced. This is in contrast to the dark sheet resistivity values, however, which increase in value with the reduction in Fe doping, corresponding to reduced over-compensation, as discussed previously.

The THz power as a function of excitation power was next measured at the intended operational wavelength of 1550 nm for emitters fabricated on wafers of three Fe concentrations ($2208_{100}$, $2213_{0.8}$, and $2321_{0.4}$) and compared to an equivalent photoconductive emitter formed on LT-GaAs excited at 800 nm. The results in FIG. 22(c) show that all Fe:InGaAs wafers outperform the LT-GaAs emitter under identical biasing conditions.

Thus, it has been demonstrated that Fe doping introduced during MOCVD growth of InGaAs produces photoconductive material capable of generating THz radiation across a wide range of excitation wavelengths, with high levels of reproducibility and control between and during wafer growth. At the highest levels of Fe doping, the material has a high density of FeAs precipitates, which has a detrimental effect on performance. However, reduction in the Fe doping improves emitter performance without sacrificing bandwidth, despite the corresponding reduction in the number of deep acceptor states and increase in (dark) dc sheet resistivity. The bandwidth achieved from these photoconductive emitters was >2 THz, primarily limited by the pulsewidth of the OPO laser used for carrier generation. In all cases, the output powers achieved at 1550 nm were larger than equivalent LT-GaAs excited at 800 nm under equivalent biasing conditions.

The invention claimed is:

1. A method of generating radiation, the method comprising:
    manufacturing a structure comprising a substrate supporting a layer of InGaAs, InGaAsP, or InGaAlAs material doped with a dopant, said manufacturing comprising growing said layer such that said dopant is incorporated in said layer during growth of the layer;
    illuminating a portion of a surface of the structure with radiation having photon energies greater than or equal to a band gap of the doped InGaAs, InGaAsP, or InGaAlAs material so as to create electron-hole pairs in the layer of doped material; and
    accelerating the electrons and holes of said pairs with an electric field so as to generate radiation.

2. A method in accordance with claim 1, wherein said dopant is an element.

3. A method in accordance with claim 1, wherein said dopant is a transition metal element.

4. A method in accordance with claim 1, wherein said dopant is chromium or vanadium.

5. A method in accordance with claim 1, wherein said dopant is Fe.

6. A method in accordance with claim 1, wherein the generated radiation comprises radiation having a frequency in the range 0.05 THz to 20 THz.

7. A method in accordance with claim 1, wherein the substrate comprises a single crystal of material.

8. A method in accordance with claim 1, wherein growing said layer comprises epitaxially growing said layer on the substrate.

9. A method in accordance with claim 1, wherein said illuminating comprises illuminating said portion with radiation having a wavelength in the range 800 nm to 1700 nm.

10. A method in accordance with claim 1, wherein said illuminating comprises illuminating said portion with radiation in a direction substantially normal to said layer.

11. A method in accordance with claim 1, wherein said illuminating comprises illuminating said portion with radiation in a direction substantially parallel to said layer.

12. A method in accordance with claim 1, further comprising applying said electric field to accelerate said electrons and holes.

13. A method in accordance with claim 8, wherein said structure comprises a first electrode and a second electrode, and applying said electric field comprises applying a potential difference between the first and second electrodes.

14. A method in accordance with claim 9, wherein said potential difference is an alternating potential difference.

15. A method in accordance with claim 13, wherein said electrodes are arranged to define a gap between them, and said illuminating comprises directing the illuminating radiation at said gap.

16. A method in accordance with claim 13, wherein said electrodes are arranged at a surface of the structure.

17. A method in accordance with claim 13, wherein said electrodes are embedded in the structure.

18. Apparatus for generating radiation, the apparatus comprising:
a structure comprising a substrate supporting a layer of InGaAs, InGaAsP, or InGaAlAs material doped with a dopant, said layer having been grown such that said dopant has been incorporated in said layer during growth of the layer; and
an illumination source arranged to illuminate a portion of a surface of the structure with radiation having photon energies greater than or equal to a band gap of the doped material so as to create electron-hole pairs in the layer of doped material.

19. Apparatus in accordance with claim 18, wherein said dopant is an element.

20. Apparatus in accordance with claim 18, wherein said dopant is a transition metal element.

21. Apparatus in accordance with claim 19, wherein said dopant is chromium or vanadium.

22. Apparatus in accordance with claim 19, wherein said dopant is Fe.

23. Apparatus in accordance with claim 18, further comprising means for applying an electric field to accelerate the electrons and holes of said pairs so as to generate radiation.

24. Apparatus in accordance with claim 23, wherein said means for applying an electric field comprises a first electrode and a second electrode, and a voltage source arranged to apply a potential difference between the first and second electrodes.

25. Apparatus in accordance with claim 18, further comprising a lens arranged to focus radiation generated by said electron-hole pairs.

26. Apparatus in accordance with claim 25, wherein the lens is arranged to focus generated radiation transmitted through the substrate.

27. Apparatus in accordance with claim 18, wherein the illumination source is adapted to illuminate said portion with radiation having a wavelength in the range 800 nm to 1700 nm.

28. Apparatus in accordance with claim 27, wherein the illumination source comprises a laser.

29. A spectroscopy method comprising:
generating radiation using a method in accordance with claim 1;
directing the generated radiation at a sample or object; and
detecting at least one of: generated radiation transmitted through; and generated radiation reflected from the sample or object.

30. Spectroscopy apparatus comprising:
apparatus in accordance with claim 18, arranged to generate radiation;
means for directing the generated radiation at a sample or object; and
detection means for detecting at least one of: generated radiation transmitted through; and generated radiation reflected from a sample or object at which the generated radiation is directed.

31. A method of detecting THz radiation comprising:
manufacturing a structure comprising a substrate supporting a layer of InGaAs, InGaAsP, or InGaAlAs material doped with a dopant, said manufacturing comprising growing said layer such that said dopant is incorporated in said layer during growth of the layer;
illuminating a portion of a surface of the structure with THz radiation to be detected and probe radiation, such that photons of said probe radiation having energies greater than or equal to a band gap of the doped material create electron-hole pairs in the layer of doped material and said electron-hole pairs are accelerated by the THz radiation; and
detecting an electric field or current generated by the accelerated electron-hole pairs.

32. A method in accordance with claim 31, wherein said structure comprises a first electrode and a second electrode, and said detecting comprises detecting a current between the first and second electrodes.

33. Apparatus for detecting THz radiation, the apparatus comprising:
a structure comprising a substrate supporting a layer of InGaAs, InGaAsP, or InGaAlAs material doped with a dopant, said layer having been grown such that said dopant has been incorporated in said layer during growth of the layer;
means for illuminating a portion of a surface of the structure with THz radiation to be detected and probe radiation, such that photons of said probe radiation having energies greater than or equal to a band gap of the doped material create electron-hole pairs in the layer of doped material and said electron-hole pairs are accelerated by the THz radiation; and
means for detecting an electric field or current generated by the accelerated electron-hole pairs.

34. Apparatus in accordance with claim 33, wherein said structure comprises a first electrode and a second electrode, and said means for detecting comprises means for detecting a current between the first and second electrodes.

35. An antenna for generating and/or detecting THz radiation, the antenna comprising:
a substrate supporting a layer of InGaAs, InGaAsP, or InGaAlAs material doped with a dopant, said layer having been grown such that said dopant has been incorporated in said layer during growth of the layer; and
a first electrode and a second electrode,
the electrodes being arranged to define a gap between them and being further arranged with respect to said layer such that when radiation is directed at said gap, photons of said radiation having energies greater than or equal to a band gap of the doped material create electron-hole pairs in the layer of doped material, and an electric field may be applied to accelerate the electron-hole pairs and generate THz radiation by application of a potential difference between the electrodes, and/or an electric current generated by the electron-hole pairs across the electrodes may be detected when the THz radiation is directed at said gap so as to accelerate the electron-hole pairs.

36. A method in accordance with claim 31, wherein said dopant is an element.

37. A method in accordance with claim 31, wherein said dopant is a transition metal element.

38. A method in accordance with claim 31, wherein said dopant is chromium or vanadium.

39. A method in accordance with claim 31, wherein said dopant is Fe.

* * * * *